US008709724B2

(12) United States Patent
Tabor et al.

(10) Patent No.: US 8,709,724 B2
(45) Date of Patent: Apr. 29, 2014

(54) ISOTHERMAL AMPLIFICATION OF DNA

(75) Inventors: Stanley Tabor, Brookline, MA (US); Charles C. Richardson, Newton, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 622 days.

(21) Appl. No.: 10/813,693

(22) Filed: Nov. 7, 2003

(65) Prior Publication Data

US 2005/0164213 A1    Jul. 28, 2005

Related U.S. Application Data

(63) Continuation of application No. 09/480,878, filed on Jan. 10, 2000, now abandoned.

(60) Provisional application No. 60/115,498, filed on Jan. 11, 1999.

(51) Int. Cl.
*C12Q 1/68* (2006.01)
*C12N 9/12* (2006.01)

(52) U.S. Cl.
USPC ......................................... 435/6.12; 435/194

(58) Field of Classification Search
None
See application file for complete search history.

(56) References Cited

U.S. PATENT DOCUMENTS

| 4,942,130 A | 7/1990 | Tabor et al. |
| 4,946,786 A | 8/1990 | Tabor et al. |
| 5,194,370 A | 3/1993 | Berninger et al. |
| 5,556,772 A * | 9/1996 | Sorge et al. .................. 435/91.2 |

FOREIGN PATENT DOCUMENTS

| EP | 0623682 | 11/1994 |
| WO | WO 96/05296 | 2/1996 |
| WO | WO 98/42689 | 10/1998 |
| WO | WO 00/41524 | 7/2000 |

OTHER PUBLICATIONS

Scherzinger et al. (Eur. J. Biochem 72, 543-558 (1977)).*
Engler et al. (The Journal of Biological Chemistry (1993), vol. 258, No. 18, pp. 11197-11203).*
Applegren et al. (Journal of Cellular Biochemistry 59:91-107 (1995)).*
Decker et al. In vitro initiation of DNA replication in Simian Virus 40 chromosomes. The Journal of Biological Chemistry. (1987) 262(22): 10863-10872.*
Biswas et al. Quantitative analysis of nucleotide modulation of DNA binding by DnaC protein of *Escherichia coli*. Biochemical Journal (2004) 379(Pt 3): 553-562.*
Dickinson et al. Nucleoside diphosphokinase and cell cycle control in the fission yeast Schizosaccharomyces pombe. Journal of Cell Science. (1983) 60: 355-365.*
Peller. Thermodynamic limits on the size and size distribution of nucleic acids synthesized in vitro: The role of pyrophosphate hydrolysis. Biochemistry (1977) 16(3): 387-395.*
Jarvis et al. "Macromolecular crowding": Thermodynamic consequences for protein-protein interactions within the T4 DNA replication complex. The Journal of Biological Chemistry (1990) 265(25): 15160-15167.*
Nakai, H. Amplification of Bacteriophage Mu DNA by rolling circle DNA replication in vitro. The Journal of Biological Chemistry. (1993) 268(32): 23997-24004.*
Lee et al. Coordinated leading and lagging strand DNA synthesis on a minicircular template. Molecular Cell (Jun. 1998) 1: 1001-1010.*
Yuzhakov et al. Replisome assembly reveals the basis for asymmetric function in leading and lagging strand replication. Cell (1996) 86: 877-886.*
Bochkarev et al. Crystal structure of the DNA-binding domain of the Epstein-Barr virus origin-binding protein, EBNA1, bound to DNA. Cell (1996) 84: 791-800.*
Walker et al. Strand displacement amplification—an isothermal, in vitro DNA amplification technique. Nucleic Acids Research (1992) 20(7): 1691-1696.*
Jeong et al. Isothermal DNA amplification in vitro: the helicase-dependent amplification system. Cell and Molecular Life Sciences (2009) 66(20): 3325-3336.*
Li et al. Primase-based whole genome amplification. Nucleic Acids Research (2008) 36(13): e79.*
Asano et al. Filamentous phage replication initiator protein gpII forms a covalent complex with the 5' end of the nick it introduced. Nucleic Acids Research (1999) 27(8): 1882-1889.*
Tabor and Richardson, "Selective Oxidation of the Exonuclease Domain of Bacteriophage T7 DNA Polymerase," J. Biol. Chem. vol. 262, No. 32, Nov. 15, pp. 15330-15333 (1987).
Almaula et al., "Nucleoside Dephosphate Kinase From *Escherichia coli*," J. Bact. 177:2524 (1995).
Applegren et al., "Further characterization of the human cell multiprotein DNA replication complex." Journal of Cellular Biochemistry 59:91-107 (1995).
Barnes, "PCR Amplification of Up to 35-Kb DNA With High Fidelity and High Yield From Bacteriophage Templates," Proc. Natl. Acad. Sci. USA 91:2216 (1994).
Beato, "Steroid hormone receptors: Many actors in search of a plot." Cell, 83:851-857, 1995.
Bernstein et al., "A 7-kDa Region of the Bacteriophage T7 Gene 4 Protein Is Required of Primase But Not for Helicase Activity," Proc. Natl. Acad. Sci. USA 85:396 (1988).
Bernstein et al., "Characterization of the Helicase and Primase Activities of the 63-Kda Component of the Bacteriophage T7 Gene 4 Protein," J. Biol. Chem. 264:13066 (1989).
Blanco et al., "Terminal Protein -Primed DNA Amplification," Proc. Natl. Acad. Sci. USA 91:12198-12202, December (1994).

(Continued)

*Primary Examiner* — Angela M Bertagna
(74) *Attorney, Agent, or Firm* — Foley & Lardner LLP

(57) ABSTRACT

A method of amplifying a template DNA molecule comprising incubating the template DNA molecule in a reaction mixture comprising a DNA polymerase and at least one accessory protein at a constant temperature to produce amplified product, wherein production of amplified product does not require exogenously-added oligonucleotide primers and the template DNA molecule does not have have terminal protein covalently bound to either 5' end.

34 Claims, 3 Drawing Sheets

(56) References Cited

OTHER PUBLICATIONS

Cheng et al., "Effective Amplification of Long Targets From Cloned Insects and Human Genomic DNA", Proc. Natl. Acm). Sci. USA 91:5695 (1994).
Cohen et al., "An Artificial Cell Cycle Inhibitor Isolated From A Combinatorial Laboratory," Proc. Natl. Acad. Sci. USA 95:14272 (1998).
Doherty et al., "Bacteriophage T7 DNA ligase." J. Biol. Chem. 271:11083 (1996).
Engler et al., "Bacteriophage T7 DNA Replication," J. Biol. Chem. 258:11197 (1983).
Engler et al., "Two Forms of the DNA Polymerase of Bacteriophage T7," J. Biol. Chem. 258:11165-11173 (1983).
Evans, The steroid and thyroid hormone receptor superfamily. Science, 240: 889-895, 1988.
Ewing et al., "Base-Calling of Automated Sequencer Traces Using Phred. II. Error Probabilities," Genome Research 8:186 (1998).
Famulok et al., Oligonucleotide libraries—variatio delectat. Curr. Opin. Chem. Biol. 2:320 (1998).
Gibson et al., "A Novel Method for Real Time Quantitative RT-PCR," (Genome Research 6:995 (1996).
Greenstein et al.,"Interaction Between the Replication Origin and the Initiator Protein of the Filamentous Phage Fl: Binding Occurs in Two Steps," J. Molec. Biol. 197:157 (1987).
Guatelli et al., "Isothermal, In Vitro Amplification of Nucleic Acids by a Multienzyme Reaction Modeled After Retro Viral Replication," Proc. Natl. Acad. Sci. USA 87:1874 (1990).
Guo et al., "The Linker Egion Between the Helicase and Primase Domains of the Bacteriophage T7 Gene 4 Protein Is Critical for Hexamer Formation," J Biol. Chem. 274:30303 (1999).
Harth et al., "Bacteriophage Fd Gene-2 Protein," Eur. J. Biochem. 119:663 (1981).
Higashitanit et al., "A Single Amino Acid Substitution Reduces the Superhelicity Requirement of a Replication Initiator Protein," Nucl. Acids Res. 20:2685 (1992).
Jesperson, T. et al., "Efficient Non-PCR-Medicated Overlap Extension of PCR-Medicated Overlap Extension of PCR Fragments by Exonuclease End Polishing", Biotechniques 23, No. 1:48-52 (1997).
Kerr et al., "Gene 6 Exonuclease of Bacteriophage T7," J Biol. Chem. 247:305 (1972).
Kim et al., "Purification and Characterization of the Bacteriophage T7 Gene 2.5 Protein," J. Biol. Chem. 267:15022(1992).
Lee et al., "Coordinated Leading and Lagging Strand DNA Synthesis on a Minicircular Template," Mol. Cell. 1:1001 (1998).
Lohman et al., "Large Scale Overproduction and Rapid Purification of the *Escherichia coli* SSB Gene Product. Expression of the SSB Gene Under PL Control, Biochemistry" (1986) vol. 25, No. 1, pp. 21-25.
Mangelsd and Evans, The RXR heterodimers and orphan receptors. Cell, 842-850, (1995) vol. 83, No. 6, pp. 841-850.
Mendelman et al., "Evidence for Distinct Primase and Helicase Domains in the 63-KDA Gene 4 Protein of Bacteriophage T7," J.Biol.Chem 268:27208 (1993).
Matson and Richardson, "DNA-Dependant Nucleoside 5'—Triphosphatase Activity of the Gene 4 Protein of Bacteriophage T7," J Biol Chem. 258:14009-14016 (1983).
Mendelman et.al., "Roles of Bacteriophage T7 Gene 4 Proteins in Providing Primase and Helicase Functions in Vivo," Proc. Natl. Acad. Sci. USA 89:10638 (1992).
Meyer et al., "Replication of Phage FD RF With FD Gene 2 Protein and Phage TF Enzymes," J. Biol. Chem. 256:58 10 (1981).
Mitra and Church, "In Situ Localized Amplification and Contact Replication of Many Individual DNA Molecules," Nucleic Acids Res. 27 (24):E34 (1999).
Notarnicola et al., "A Domain of the Gene 4 Helicase/Primase of Bacteriophage T7 Required for the Formation of an Active Hexamer," J. Biol. Chem 273:5260 (1998).
Notarnicola et al., "The Nucleotide Binding Site of the Helicase/Primase of Bacteriphage T7," J. Biol. Chem. 268:27198 (1993).
Park et al., "Formation of a DNA Loop at the Replication Fork Generated by Bacteriophage T7 Replication Proteins," J. Biol. Chem. 273:5260 (1998).
Saiki et al., "Enzymatic Amplification of B-Globin Genomic Sequences and Restriction Site Analysis for Diagnosis of Sickle Cell Anemia," Science 230:1350-1354 (1985).
Saiki et al., "Primer-Directed Enzymeatic Amplification of DNA With a Thermosatble DNA Polymerase," Science 239:487-49 1 (1988).
Salas, "Protein Priming of DNA Replication," Ann. Rev. Biochem 60:39 (1991).
Sarkar et al., "Removal of DNA contamination in polymerase chain reaction reagents by ultraviolet irradiation." Methods of Enzymology, 218:38 1-388 (1993).
Scherzinger et al., "Role of Bacteriophage T7 DNA Primase in the Initiation of DNA Strand Synthesis," Nucl. Acids Res. 4:4151 (1977).
Scherzinger et al., Bacteriophage-T7-induced DNA-priming protein : A novel enzyme involved in DNA replication. Eur. J. Biochem 72:543-558 (1977).
Tabor et al., "*Eschericia coli* Thioredoxin Confers Processivity on the DNA Polymerase Activity of the Gene 5 Protein of Bacteriophage T7," J. Biol. Chem. 262:16212-16223 (1987).
Tabor et al., "Selective Inactivation of the Exonuclease Activity of Bacteriophage T7 DNA Polymerase by in Vitro Mutagenesis," J. Biol. Chem. 262:6447-6458 (1989).
Tabor et al., "DNA Sequence Analysis with a Modified Bacteriophage T7 DNA Polymerase." Journal of Biological Chemistry 265(14):8322-8328 (1990).
Tyagi et al., "Extremely Sensitive Background-Free Gene Detection Using Binary Probes and QB Replicase," Proc. Natl. Acad. Sci. USA 93:5395 (1996).
Walker et al., "Isothermal in Vitro Amplification of DNA by a Restriction Enzyme/DNA Polymerase System," Proc. Natl. Acad. Sci. USA 89:392 (1992).
Werle *Laboratory Methods for the Detection of Mutations and Polymorphisms in DNA*, ed. Taylor "Direct Sequencing of Polymerase chain reaction products." pp. 163-174 (1997).
Zhang et al., "Amplification of Target-Specific, Ligation-Dependant Circular Probe," Gene 211:277 (1998).

\* cited by examiner

FIG. 1A

```
         |  10        |  20        |  30        |  40        |  50        |  60        |  70        |  80
    ATGGACAATT CGCACGATTC CGATAGTGTA TTTCTTTACC ACATTCCTTG TGACAACTGT GGGAGTAGTG ATGGGAACTC  80
    GCTGTTCTCT GACGGACACA CGTTCTGCTA CGTATGCGAG AAGTGGACTG CTGGTAATGA AGACACTAAA GAGAGGGCTT  160
    CAAAACGGAA ACCCTCcGGt GGaAAgCCcg gGACTTACAA CGTGTGGAAC TTCGGGGAAT CCAATGGACG CTACTCCGCG  240
    TTAACTGCGA GAGGAATCTC CAAGGAAACC TGTCAGAAGG CTGGCTACTG GATTGCCAAA GTAGACGGTG TGATGTACCA  320
    AGTGGCTGAC TATCGGGACC AGAACGGCAA CATTGTGAGT CAGAAGGTTC GAGATAAAGA TAAGAACTTT AAGACCACTG  400
    GTAGTCACAA GAGTGACGCT CTGTTCGGGA AGCACTTGTG GAATGGTGGT AAGAAGATTG TCGTTACAGA AGGTGAAATC  480
    GACATGCTTA CCGTGATGGA ACTTCAAGAC TGTAAGTATC CTGTAGTGTC GTTGGGTCAC GGTGCCTCTG CCGCTAAGAA  560
    CACATGCGCT GCCAACTACG AATACTTTGA CCAGTTCGAA CAGATTATCT TAATGTTCGA TATGGACGAA GCAGGGCGCA  640
    AAGCAGTCGA AGAGGCTGCA CAGGTTCTAC CTGCTGGTAA GGTACGAGTG GCAGTTCTTC CGTGTAAGGA TGCAAACGAG  720
    TGTCACCTAA ATGGTCACGA CCGTGAAATC ATGGAGCAAG TGTGGAATGC TGGTCCTTGG ATTCCTGATG GTGTGGTATC  800
    GGCTCTTTCG TTACGTGAAC GAATCCGTGA GCACCTATCG TCCGAGGAAT CAGTAGGGTT ACTTTTCAGT GGCTGCACTG  880
    GTATCAACGA TAAGACCTTA GGTGCCCGTG GTGGTGAAGT CATTATGGTC ACTTCCGGTT CCGGTATGCG TAAGTCAACG  960
    TTCGTCCGTC AACAAGCTCT ACAATGGGGC ACAGCGATGG GCAAGAAGGT AGGCTTAGCG ATGCTTGAGG AGTCCGTTGA  1040
    GGAGACCGCT GAGGACCTTA TAGGTCTACA CAACCGTGTC CGACTGAGAC AATCCGACTC ACTAAACAGA GAGATTATTG  1120
    AGAACGGTAA GTTCGACCAA TGGTTCGATG AACTGTTCGG CAACGATACG TTCCATCTAT ATGACTCATT CGCCGACGCT  1200
    GAGACGGATA GACTGCTCGC TAAGCTGCC TACATGCGCT CAGGCTTGGG CTGTGACGTA ATCATTCTAG ACCACATCTC  1280
    AATCGTCGTA TCCGCTTCTG GTGAATCCGA TGAGCGTAAG ATGATTGACA ACCTGATGAC CAAGCTCAAA CGGTTCGCTA  1360
    AGTCAACTGG GGTGGTGCTG GTCGTAATTT GTCACCTTAA GAACCCAGAC AAAGGTAAAG CACATGAGGA AGGTCGCCCC  1440
    GTTTCTATTA CTGACCTACG TGGTTCTGCC GCACTACGCC AACTATCTGA TACTATTATT GCCCTTGAGC GTAATCAGCA  1520
    AGGCGATATG CCTAACCTTG TCCTCGTTCG TATTCTCAAG TGCCCGTTTA CTGGTGATCA TGGTATCGCT GGCTACATGG  1600
    AATACAACAA GGAAACCGGA TGGCTTGAAC CATCAAGTTA CTCAGGGGAA GAAGAGTCAC ACTCAGAGTC AACAGACTGG  1680
    TCCAACGACA CTGACTTCTG ACAGGATTCT TGATGACTTT CCAGACGACT ACGAGAAGTT TGCTGGAGA GTCCCATTCT  1760
    AATACGACTC ACTAAAGGAG ACACACCATG TTCAAACTGA TTAAGAAGTT AGGCCAACTG CTGGTTCGTA TGTACAACGT  1840
    GGAAGCCAAG CGACTGAACG ATGAGGCTCG TAAAGAGGCC ACACAGTCAC GCGCTCTGCC GATTCGCTCC AAAACTGGTT  1920
    TTGCGCTTAC CCCAACCAAC AGGGGATTTG CTGCTTTCCA TTGAGCCTGT TTCTCTGCGC GACGTTCGCG GCGGCGTGTT  2000
    TGTGCATCCA TCTGGATTCT CCTGTCACTT AGCTTTCGTC GTGTGTGGCA GTTGTAGTCC TGAACGAAAA CCCCCGGCGA  2080
    TTGGCACATT GGCAGCTAAT CCGGAATCGC ACTTACGGCC AATGCTTCGT TTCGTATCAC ACACCCCAAA GCCTTCTGCT  2160
    TTGAATGCTG CCCTTCTTCA CGGCTTAATT TTTAAGAGCG TCACCTTCAT GGTGGTCAGT GCCTCCTGCT GATGTGCTCA  2240
    GTATCACCGC CAGTGGTATT TATGTCAACA CCGCCAGAGA TAATTTATCA CGGCAGATGC TTATCTGTAT GTTTTTTATA  2320
    TGAATTTATT TTTTGCAGGG GGGCATTGTT TGGTAGGTGA GAGATCCGGC TGCTAACAAA GCCCGAAAGG AAGCTGAGTT  2400
    GGCTGCTGCC ACCGCTGAGC AATAACTAGC ATAACCCCTT GGGGCCTCTA AACGGGTCTT GAGGGGTTTT TTGCTGAAAG  2480
    GAGGAACTAT ATCCGGATAT CCCGCAAGAG GCCCGCCAGT ACCGGCATAA CCAAGCCTAT GCCTACAGCA TCCAGGGTGA  2560
    CGGTCCCGAG GATGACGATG AGCCATTGT TAGATTTCAT ACACGGTGCC TGACTGCGTT AGCAATTTAA CTGTGATAAA  2640
    CTACCGCATT AAAGCTTGCG GCCGCACTCG ACGAACCCTT CGGATCTCGA TCCCGCGAAA TTAATACGAC TCACTATAGG  2720
    GAGACCACAA CGGTTTCCCT CTAGAAATAA TTTTGTTTAA CTTTAAGAAG GAGATATACA TATGCGTGAA CGAATCCGTC  2800
    AGCACCTATC GTCCGAGGAA TCAGTAGGTT TACTTTTCAG TGGCTGCACT GGTATCAACG ATAAGACCTT AGGTGCCCGT  2880
    GGTGGTGAAG TCATTATGGT CACTTCCGGT TCCGGTATGC GTAAGTCAAC GTTCGTCCGT CAACAAGCTC TACAATGGGG  2960
    CACAGCGATG GGCAAGAAGG TAGGCTTAGC GATGCTTGAC GAGTCCGTTG AGGAGACCGC TGAGGACCTT ATAGGTCTAC  3040
    ACAACCGTGT CCGACTGAGA CAATCCGACT CACTAAAGAG AGAGATTATT GAGAACGGTA AGTTCGACCA ATGGTTCGAT  3120
    GAACTGTTCG GCAACGATAC GTTCCATCTA TATGACTCAT TCGCCGAGGC TGAGACGGAT AGACTGCTCG CTAAGCTGGC  3200
    CTACATGCGC TCAGGCTTGG GCTGTGACGT AATCATTCTA GACCACATCT CAATCGTCGT ATCCGCTTCT GGTGAATCCG  3280
    ATGAGCGTAA GATGATTGAC AACCTGATGA CCAAGCTCAA AGGGTTCGCT AAGTCAACTG GGGTGGTGCT GGTCGTAATT  3360
    TGTCACCTTA AGAACCCAGA CAAAGGTAAA GCACATGAGG AAGGTCGCCC CGTTTCTATT ACTGACCTAC GTGGTTCTGG  3440
    CGCACTACGC CAACTATCTG ATACTATTAT TGCCCTTGAG CGTAATCAGC AAGGCCATAT GCCTAACCTT GTCCTCGTTC  3520
```

FIG. 1B

```
GTATTCTCAA GTGCCGCTTT ACTGGTGATA CTGGTATCGC  TGGCTACATG GAATACAACA AGGAAACCGG ATGGCTTGAA 3600
CCATCAAGTT ACTCAGGGGA AGAAGAGTCA CACTCAGAGT  CAACAGACTG GTCCAACGAC ACTGACTTCT GAGGATCCAC 3680
TAGTAACGGC CGCCAGTGTG CTGGAATTCT GCAGATATCC  ATCACACTGG CGGCCGCTCG AGCACCACCA CCACCACCAC 3760
TGAGATCCGG CTGCTAACAA AGCCCGAAAG GAAGCTGAGT  TGGCTGCTGC CACCGCTGAG CAATAACTAG CATAACCCCT 3840
TGGGGCCTCT AAACGGGTCT TGAGGGGTTT TTTGCTGAAA  GGAGGAACTA TATCCGGATT GGCGAATGGG ACGCGCCCTG 3920
TAGCGGCGCA TTAAGCGCGG CGGGTGTGGT GGTTACGCGC  AGCGTGACCG CTACACTTGC CAGCGCCCTA GCGCCCGCTC 4000
CTTTCGCTTT CTTCCCTTCC TTTCTCGCCA CGTTCGCCGG  CTTTCCCCGT CAAGCTCTAA ATCGGGGGCT CCCTTTAGGG 4080
TTCCGATTTA GTGCTTTACG GCACCTCGAC CCCAAAAAAC  TTGATTAGGG TGATGGTTCA CGTAGTGGGC CATCGCCCTG 4160
ATAGACGGTT TTTCGCCCTT TGACGTTGGA GTCCACGTTC  TTTAATAGTG GACTCTTGTT CCAAACTGGA ACAACACTCA 4240
ACCCTATCTC GGTCTATTCT TTTGATTTAT AAGGGATTTT  GCCGATTTCG GCCTATTGGT TAAAAAATGA GCTGATTTAA 4320
CAAAAATTTA ACGCGAATTT TAACAAAATA TTAACGTTTA  CAATTTCAGG TGGCACTTTT CGGGGAAATG TGCGCGGAAC 4400
CCCTATTTGT TTATTTTTCT AAATACATTC AAATATGTAT  CCGCTCATGA ATTAATTCTT AGAAAAACTC ATCGAGCATC 4480
AAATGAAACT GCAATTTATT CATATCAGGA TTATCAATAC  CATATTTTTG AAAAAGCCGT TTCTGTAATG AAGGAGAAAA 4560
CTCACCGAGG CAGTTCCATA GGATGGCAAG ATCCTGGTAT  CGGTCTGCGA TTCCGACTCG TCCAACATCA ATACAACCTA 4640
TTAATTTCCC CTCGTCAAAA ATAAGGTTAT CAAGTGAGAA  ATCACCATGA GTGACGACTG AATCCGGTGA GAATGGCAAA 4720
AGTTTATGCA TTTCTTTCCA GACTTGTTCA ACAGGCCAGC  CATTACGCTC GTCATCAAAA TCACTCGCAT CAACCAAACC 4800
GTTATTCATT CGTGATTGCG CCTGAGCGAG ACGAAATACG  CGATCGCTGT TAAAAGGACA ATTACAAACA GGAATCGAAT 4880
GCAACCGGCG CAGGAACACT GCCAGCGCAT CAACAATATT  TTCACCTGAA TCAGGATATT CTTCTAATAC CTGGAATGCT 4960
GTTTTCCCGG GGATCGCAGT GGTGAGTAAC CATGCATCAT  CAGGAGTACG GATAAAATGC TTGATGGTCG GAAGAGGCAT 5040
AAATTCCGTC AGCCAGTTTA GTCTGACCAT CTCATCTGTA  ACATCATTGG CAACGCTACC TTTGCCATGT TTCAGAAACA 5120
ACTCTGGCGC ATCGGGCTTC CCATACAATC GATAGATTGT  CGCACCTGAT TGCCCGACAT TATCGCGAGC CCATTTATAC 5200
CCATATAAAT CAGCATCCAT GTTGGAATTT AATCGCGGCC  TAGAGCAAGA CGTTTCCCGT TGAATATGGC TCATAACACC 5280
CCTTGTATTA CTGTTTATCT AACCAGACAC TTTTATTGTT  CATGACCAAA ATCCCTTAAC GTCACTTTTC CTTCCACTGA 5360
GCGTCAGACC CCGTAGAAAA GATCAAAGGA TCTTCTTGAG  ATCCTTTTTT TCTGCGCGTA ATCTGCTGCT TGCAAACAAA 5440
AAAACCACCG CTACCAGCGG TGGTTTGTTT GCCGGATCAA  GAGCTACCAA CTCTTTTTCC GAAGGTAACT GGCTTCAGCA 5520
GAGCGCAGAT ACCAAATACT GTCCTTCTAG TGTAGCCGTA  GTTAGGCCAC CACTTCAAGA ACTCTGTAGC ACCGCCTACA 5600
TACCTCGCTC TGCTAATCCT GTTACCAGTG GCTGCTGCCA  GTGGCGATAA GTCGTGTCTT ACCGGGTTGG ACTCAAGACG 5680
ATAGTTACCG GATAAGGCGC AGCGGTCGGG CTGAACGGGG  GGTTCGTGCA CACAGCCCAG CTTGGAGCGA ACGACCTACA 5760
CCGAACTGAG ATACCTACAG CGTGAGCTAT GAGAAAGCGC  CACGCTTCCC GAAGGGAGAA AGGCGGACAG GTATCCGGTA 5840
AGCGGCAGGG TCGAACAGGG AGACCGCACC AGGGAGCTTC  CAGGGGGAAA CGCCTGGTAT CTTTATAGTC CTGTCGGGTT 5920
TCGCCACCTC TGACTTGAGC GTCGATTTTT GTGATGCTCG  TCAGGGGGGC GGAGCCTATG GAAAAACGCC AGCAACGCGG 6000
CCTTTTTACG GTTCCTGGCC TTTTGCTGGC CTTTTGCTCA  CATGTTCTTT CCTGCGTTAT CCCCTGATTC TGTGGATAAC 6080
CGTATTACCG CCTTTGAGTG AGCTGATACC GCTCGCCGCA  GCCGAACGAC CGAGCGCAGC GAGTCAGTGA GCGAGGAAGC 6160
GGAAGAGCGC CTGATCCGGT ATTTTCTCCT TACGCATCTC  TGCCGTTTCC CACACCGCAT ATATGGTGCA CTCTCAGTAC 6240
AATCTGCTCT GATGCCGCAT AGTTAAGCCA GTATACACTC  CGCTATCGCT ACGTGACTGG GTCATGGCTG CGCCCCGACA 6320
CCCGCCAACA CCCGCTGACG CGCCCTGACG GGCTTGTCTG  CTCCCGGCAT CCGCTTACAG ACAAGCTGTG ACCGTCTCCG 6400
GGAGCTGCAT GTGTCAGAGG TTTTCACCGT CATCACCGAA  ACGCGCGAGG CAGCTGCGGT AAAGCTCATC AGCGTGGTCG 6480
TGAAGCGATT CACAGATGTC TGCCTGTTCA TCCGCGTCCA  GCTCGTTGAG TTTCTCCAGA AGCGTTAATG TCTGCTTCT 6560
GATAAAGCGG GCCATGTTAA GGGCGGTTTT TTCCTGTTTG  GTCACTGATG CCTCCGTGTA AGGGGGATTT CTGTTCATGG 6640
GGGTAATGAT ACCGATGAAA CGAGAGAGGA TGCTCACGAT  ACGGGTTACT GATGATGAAC ATGCCCGGTT ACTGGAACGT 6720
TGTGAGGGTA AACAACTGGC GGTATGGATG CGGCGGGACC  AGAGAAAAAT CACTCAGGGT CAATGCCAGC GCTTCGTTAA 6800
TACAGATGTA GGTGTTCCAC AGGGTAGCCA GCAGCATCCT  GCGATGCAGA TCCGGAACAT AATGGTGCAG GGCGCTGACT 6880
TCCGCGTTTC CAGACTTTAC GAAACACGGA AACCGAAGAC  CATTCATGTT GTTGCTCAGG TCGCAGACGT TTTGCAGCAG 6960
CAGTCGCTTC ACGTTCGCTC GCGTATCGGT GATTCATTCT  GCTAACCAGT AAGGCAACCC CGCCAGCCTA GCCGGGTCCT 7040
CAACGACAGC AGCACCATCA TGCGCACCCG TGGGGCCGCC  ATGCCGGCGA TAATGGCCTG CTTCTCGCCG AAACGTTTGG 7120
TGGCGGGACC AGTGACGAAG GCTTGAGCGA GGGCGTGCAA  GATTCCGAAT ACCGCAAGCG ACAGGCCGAT CATCGTCGCG 7200
CTCCAGCGAA AGCGGTCCTC GCCGAAAATG ACCCAGAGCG  CTGCCGGCAC CTGTCCTACG AGTTGCATGA TAAAGAAGAC 7280
AGTCATAAGT GCGGCGACGA TAGTCATGCC CCGCGCCCAC  CGGAAGGAGC TGACTGGGTT GAAGGCTCTC AAGGGCATCG 7360
GTCGAGATCC CGGTGCCTAA TGAGTGAGCT AACTTACATT  AATTGCGTTG CGCTCACTGC CCGCTTTCCA GTCGGGAAAC 7440
CTGTCGTGCC AGCTGCATTA ATGAATCGGC CAACGCGCGG  GGAGAGGCGG TTTGCGTATT GGGCGCCACC GTGGTTTTTC 7520
TTTTCACCAC TGAGACGGGC AACAGCTGAT TGCCCTTCAC  CGCCTGGCCC TGAGAGAGTT GCAGCAAGCG GTCCACGCTG 7600
GTTTGCCCCA GCAGGCGAAA ATCCTGTTTG ATGGTGGTTA  ACGGCGGGAT ATAACATGAG CTGTCTTCGG TATCGTCGTA 7680
TCCCACTACC GAGATATCCG CACCAACGCG CAGCCCGGAC  TCGGTAATGG CGCGCATTGC GCCCAGCGCC ATCTGATCGT 7760
TGGCAACCAG CATCGCAGTG GGAACGATGC CCTCATTCAG  CATTTGCATG GTTTGTTGAA AACCGGACAT GGCACTCCAG 7840
```

FIG. 1C

```
TCGCCTTCCC GTTCCGCTAT CGGCTGAATT TGATTGCGAG TGAGATATTT ATGCCAGCCA GCCAGACGCA GACGCGCCGA 7920
GACAGAACTT AATGGGCCCG CTAACAGCGC GATTTGCTGG TGACCCAATG CGACCAGATG CTCCACGCCC AGTCGCGTAC 8000
CGTCTTCATG GGAGAAAATA ATACTGTTGA TGGGTGTCTG GTCAGAGACA TCAAGAAATA ACGCCGGAAC ATTAGTGCAG 8080
GCAGCTTCCA CAGCAATGGC ATCCTGGTCA TCCAGCGGAT AGTTAATGAT CAGCCCACTG ACGCGTTGCG CGAGAAGATT 8160
GTGCACCGCC GCTTTACAGG CTTCGACGCC GCTTCGTTCT ACCATCGACA CCACCACGCT GGCACCCAGT TGATCGGCGC 8240
GAGATTTAAT CGCCGCGACA ATTTGCGACG GCGCGTGCAG GGCCAGACTG GAGGTGGCAA CGCCAATCAG CAACGACTGT 8320
TTGCCCGCCA GTTGTTGTGC CACGCGCTTG GGAATGTAAT TCAGCTCCGC CATCGCCGCT TCCACTTTTT CCCGCGTTTT 8400
CGCAGAAACG TGGCTGGCCT GGTTCACCAC GCGGGAAACG GTCTGATAAG AGACACCGGC ATACTCTGCG ACATCGTATA 8480
ACGTTACTGG TTTCACATTC ACCACCCTGA ATTGACTCTC TTCCGGGCGC TATCATCCCA TACCGCGAAA GGTTTTGCGC 8560
CATTCGATGG TGTCCGGGAT CTCGACGCTC TCCCTTATGC GACTCCTGCA TTAGGAAGCA GCCCAGTAGT AGGTTGAGGC 8640
CGTTGAGCAC CGCCGCCGCA AGGAATGGTG CATGCAAGGA GATGGCGCCC AACAGTCCCC CGGCCACGGG GCCTGCCACC 8720
ATACCCACGC CGAAACAAGC GCTCATGAGC CCGAAGTGGC GAGCCCGATC TTCCCCATCG GTGATGTCGG CGATATAGGC 8800
GCCAGCAACC GCACCTGTGG CGCCGGTGAT GCCGCCACG ATGCGTCCGG CGTAGAGGAT CGAGATCTCG ATCCCGCGAA 8880
ATTAATACGA CTCACTATAG GGGAATTGTG AGCGGATAAC AATTCCCCTC TAGAAATAAT TTTGTTTAAC TTTAAGAAGG 8960
AGATATACAT                                                                          8970
```

ISOTHERMAL AMPLIFICATION OF DNA

RELATED APPLICATIONS

This application is a continuation of U.S. application Ser. No. 09/480,878, filed Jan. 10, 2000, now abandoned, which claims the benefit of U.S. Provisional Application No. 60/115,498, filed Jan. 11, 1999, entitled ISOTHERMAL AMPLIFICATION OF DNA, both of which are incorporated by reference in their entireties, including drawings.

This invention was made with government support including a grant from the U.S. Dept. of Energy, contract number DE-FG02-96ER62251. The U.S. government may have certain rights in the invention.

FIELD OF THE INVENTION

The present invention relates to the field of amplification of DNA and RNA.

BACKGROUND OF THE INVENTION

The following is a discussion of the relevant art, none of which is admitted to be prior art to the appended claims.

A variety of methods have been developed to efficiently amplify DNA using purified proteins. These generally can be classified as ones that use thermocycling of the reaction mixtures and ones in which the reactions are isothermal. Methods that use thermocycling of the reaction mixture are based on the polymerase chain reaction, or PCR (Saiki et al., Science 230:1350, 1985). In PCR, two primers are added to the target DNA, such that the two primers are complementary to opposite strands of the target sequence with their 3' ends oriented towards one another. Multiple cycles of denaturation of target DNA, annealing of the two primers, and then extension of the primers with a DNA polymerase, results in an exponential synthesis of the target DNA sequence located between the two primers. This procedure requires the use of a DNA polymerase that is thermostable in order to survive the high temperatures required to denature the product DNA each cycle. The most common polymerase used for PCR is from Thermus aquaticus, or Taq DNA polymerase (Saiki et al., Science 239:487, 1988). Modification of the reaction conditions and the enzyme mixture used can allow the amplification of DNA up to 50 kbp in length (Barnes, Proc. Natl. Acad. Sci. USA 91:2216, 1994 and Cheng et al., Proc. Natl. Acad. Sci. USA 91:5695, 1994).

Isothermal procedures for the amplification of nucleic acid include (1) Qβ replicase, (2) self-sustained sequence replication (3SR), (3) strand displacement amplification (SDA), (4) terminal protein-primed DNA amplification using Ø29 DNA polymerase, and (5) rolling circle amplification (RCA).

The RNA-dependent RNA polymerase Qβ polymerase has been used for gene detection in a strategy that uses two probes that hybridize to adjacent positions on a target sequence that are then ligated to form an amplifiable reporter RNA (Tyagi et al., Proc. Natl. Acad. Sci. USA 93:5395, 1996).

Self-sustained sequence replication (3SR) is a method of amplifying RNA that depends on the action of three enzymes; reverse transcriptase, DNA-dependent RNA polymerase and ribonuclease H (Guatelli et al., Proc. Natl. Acad. Sci. USA 87:1874, 1990).

Strand displacement amplification (SDA) is a DNA amplification system that uses a restriction enzyme to introduce specific nicks in a target to be amplified and a DNA polymerase that is capable of strand displacement synthesis (Walker et al., Proc. Natl. Acad. Sci. USA 89:392, 1992).

Terminal protein-primed DNA amplification exponentially amplifies linear Ø29 DNA using the Ø29 proteins DNA polymerase, terminal protein, double-stranded DNA binding protein, and single-stranded DNA binding protein (Blanco et al., Proc. Natl. Acad. Sci. USA 91:12198, 1994). To date this method has only been successful using linear Ø29 DNA as template.

Rolling circle amplification (RCA) can either be linear or exponential amplification of circular oligonucleotide probes that use two primers that anneal to each of the two strands, and a DNA polymerase that strand displaces (Lizardi et al., Nature Genetics 19:225, 1998 and Zhange et al., Gene 211: 277, 1998).

In order to be used as a generalized amplification system, all of these methods require the addition of specific oligonucleotide primers that are extended by a polymerase; the primers serve to fix the limits of the segment of nucleic acid to be amplified.

SUMMARY OF THE INVENTION

The present invention provides an in vitro method to amplify DNA exponentially at a constant temperature and without the use of exogenously added primers by using a DNA polymerase and various accessory proteins. The accessory proteins function with the DNA polymerase to carry out amplification under these conditions.

In one aspect, the method involves the addition of a mixture of enzymes including a DNA polymerase, a helicase and a primase and single-stranded binding protein to template DNA, which can result in amplification of the template DNA of at least 10-fold and up to and greater than 1 million-fold amplification. Such an amplification system is useful for common molecular biology procedures, including but not limited to, the preparation of plasmid DNA from cells for DNA sequencing, cloning, providing substrates for transcription/translation reactions, and mutagenesis. In addition, this generalized system for DNA amplification can serve as a useful way to prepare large amounts of human genomic DNA from small samples for genotype analysis. This could be important both for preserving or "immortalizing" small amounts of rare DNA samples, and for more general use in clinical applications as a way to avoid removing large amounts of blood from patients to obtain DNA for genotyping. Finally, this amplification system provides a very sensitive detection system for DNA contamination in samples, for example in enzymes that have been purified under good manufacturing protocol (GMP) for use in human therapeutics.

One way in which the present invention is distinguished from other exponential procedures for amplification is that it does not require the use of exogenous oligonucleotide primers. Exogenous oligonucleotide primers refer to small nucleic acid molecules that are generally in the range of 6 to 50 bases in length, although longer primers can work. They are normally synthesized by chemical as opposed to enzymatic methods. The primers are complementary to certain regions of the template and are utilized by the polymerase to initiate DNA synthesis. The region of the template that is amplified is defined by the primers utilized. Primers are required in the present invention, however they are made by one of the components of the system, the primase, e.g., gene 4 protein, rather than being synthesized in advance and then added to the system. The addition of primers to the system of the present invention has little effect on increasing the rate of DNA synthesis (generally less than two-fold), as the system works very well even without exogenous primers. Thus, even if the replication system of the present invention contains exogenous primers, there is still substantial DNA synthesis that is exponential in nature that is independent of the primers. One of ordinary skill in the art would readily be able to distinguish DNA synthesis carried out by the claimed method from exogenously added primer dependent synthesis. In the situation where DNA synthesis is dependent on specific exogenously added primers, a new set of primers will be required for each new DNA template amplified. In the situation where DNA synthesis is dependent on the exogenous addition of random primers (e.g. random hexamers) the DNA synthesis will not be exponential. This invention describes a system whereby DNA synthesis is exponential even in the absence of any exogenously added primers.

The template DNA used in this invention also does not need have a terminal protein bound to either 5' end. A terminal protein is a protein like the type used in the bacteriophage Ø29 replication system, e.g., phage Ø29 the gene 3 protein (Salas, *Ann. Rev. Biochem.* 60:39, 1991). Such a terminal protein may be present but is not functionally required for the amplification system to work.

The term "constant temperature" refers to an amplification reaction that is carried out under isothermal conditions as opposed to thermocycling conditions. Thermocycling conditions are used by polymerase chain reaction methods in order to denature the DNA and anneal new primers after each cycle. Constant temperature procedures rely on other methods to denature the DNA, such as the strand displacement ability of some polymerases or of DNA helicases that act as accessory proteins for some DNA polymerases. Thus, the term "constant temperature" does not mean that no temperature fluctuation occurs, but rather indicates that the temperature variation during the amplification process is not sufficiently great to provide the predominant mechanism to denature product/template hybrids. Preferably the constant temperature is less than 60° C., more preferably less than 50°, still more preferably less than 45°, and can even be less than 40° C.

The constant temperature amplification is carried out "in vitro", meaning that the reaction is not carried out in cells. Generally the amplification is performed using purified or at least substantially purified proteins.

In a preferred embodiment the DNA polymerase is from a bacteriophage. Further preferred is that the DNA polymerase is from bacteriophage T7. An even further preferred embodiment is that the DNA polymerase is a mixture of enzymes including both the wild-type DNA polymerase from bacteriophage T7 as well as a mutant T7 DNA polymerase that lacks its 3' to 5' exonuclease activity. It is also preferred that the reaction mixture contains a helicase or a primase. The helicase and primase are preferably the gene 4 protein of bacteriophage T7, most preferably the 63-kDa T7 gene 4 protein that encodes the helicase/primase complex. Also preferred in the reaction mixture is a single-stranded DNA binding protein, preferably a single-stranded DNA binding protein from *Escherichia coli*.

Applicant has surprisingly found that such a combination of proteins results in an unexpectedly large amount of DNA synthesis, and that the kinetics of this DNA synthesis is exponential rather than linear in nature. By exponential it is meant that at some period of time during the reaction the rate of DNA synthesis increases. In other words, the amount of DNA synthesized at a particular time will be greater than twice the amount of DNA synthesized at half the time. For example, if the amount of DNA synthesized after 20 minutes is ten times the amount of DNA synthesized after 10 minutes, then the kinetics of DNA synthesis is exponential. On the other hand, if the amount of DNA synthesized after 20 minutes is only twice the amount of DNA synthesized after 10 minutes, then the kinetics of DNA synthesis is linear. In order to test for whether DNA synthesis is linear or exponential, a small amount of radioactive deoxynucleoside triphosphate can be added to the mixture; e.g. example, one million cpm of $[\alpha\text{-}^{32}P]dATP$ in a 50 µl reaction, or a specific activity of 40 cpm per pmol of dATP if the dATP concentration is 500 µM. Once the reaction is initiated by the addition of the enzyme mixture, aliquots are removed at varying times and the amount of DNA synthesized is determined, as described in Example 1. For example, 5 µl aliquots could be removed at 0, 1, 2, 4, 8, 16 and 32 min (although the amount of each aliquot removed and the times can vary). The amount of DNA synthesized at the different times is plotted as a function of the time of the reaction. If DNA synthesis is exponential, then the shape of the plot will be sigmoidal with the slope of the curve increasing over some portion of the time interval. A reaction will be exponential only for a portion of the time; the dNTPs will be rapidly used and the rate of new DNA synthesis will then rapidly decrease. Thus to determine if a reaction is exponential it is important to inspect the kinetics of DNA synthesis over a broad range of time (for example, from 0 to 30 min), and determine if the rate of DNA synthesis increases over any period of the time of the reaction. Also, the total amount of DNA synthesized is quite large, typically at least 10-fold more than the amount of template added to the reaction mixture, and preferably is at least 100-fold greater, or at least 1000-fold greater, or at least 10,000-fold greater, or at least 100,000-fold greater, or at least 1,000,000-fold greater, or at least 10,000,000-fold greater or even more. Thus, one unique feature of the present invention is that synthesis is both exponential and results in the production of a large amount of DNA, e.g. 10-100 times or more greater than the amount of template. Furthermore as the present invention does not require the use of exogenously added primers specific for each template being amplified, it provides a generalized amplification method not limited to the region of the DNA template delineated by primers.

Another very effective method of monitoring the amount of DNA synthesized using the isothermal exponential amplification system is to use fluorescent probes or fluorescent dyes such as SYBR Green II (Molecular Probes, Eugene, Oreg.) to continuously report the amount of DNA in the reaction in real time. The basic principle of this method has been used successfully to determine the initial concentrations of specific RNAs and DNAs in a PCR reaction (Gibson et al., *Genome Research* 6:995, 1996). Fluorescence can be monitored at intervals of 15 seconds using fluorescence-based real-time PCR instruments such as the PE Biosystems 5700 (PE Biosystems, Foster City, Calif.), the Roche LightCycler (Indianapolis, Ind.), or fluorescence microtiter plate readers that can maintain a constant temperature and can carry out kinetic measurements such as the SPECTRAmax (Molecular Devices, Sunnyvale, Calif.).

A preferred embodiment for amplification of a plasmid template utilizes a polymerase in the reaction mixture such that the production of amplified product does not require exogenously-added oligonucleotide primers, the amplification is exponential, and the amount of amplified product is at least 10-fold greater than the amount of plasmid template DNA put into the reaction mixture. More preferably the amplified product is at least 100-fold greater or 1,000-fold greater, even more preferably at least 10,000-fold greater or 100,000-fold greater, and most preferably at least 1,000,000-fold greater or 10,000,000-fold greater.

The present invention also concerns the use of other reagents that further enhance amplification carried out by a core set of enzymes (the DNA polymerase, the helicase, the primase and the single-stranded binding protein). Thus, in further preferred embodiments the amplification reaction mixture also includes one or more of the following:a single-stranded binding protein of bacteriophage T7 (gene 2.5 protein), a nucleoside diphosphokinase such as that from E. coli, inorganic pyrophosphatase such as that from E. coli, an ATP regeneration system such as the combination of creatine kinase and phosphocreatine, a 5' to 3' exonuclease, preferably the 5' to 3' exonuclease is the bacteriophage T7 gene 6 exonuclease, and a ligase, preferably the ligase is the bacteriophage T7 DNA ligase. In another preferred embodiment the invention features the addition of chemical additives to the reaction mixture that increase the efficiency of the amplification reaction. Three examples of such additives are potassium glutamate, DMSO, and dextran polymer.

In another preferred embodiment the invention features the treatment of the enzymes prior to inclusion in the reaction mixture with UV irradiation in order to reduce the amplification that arises from the contaminating DNA in the enzyme preparations. Preferably the ultraviolet light is a dose from 10 to 1000 $\mu W/cm^2$, or preferably 100 to 1000 $\mu W/cm^2$, for from 15 sec to 15 min.

In other preferred embodiments, the amplification of the DNA is exponential, the DNA molecule to be amplified can range in size from 1,000 bp, to 2,000 bp, 3,000 bp, 5,000 bp, 10,000 bp, or even larger, up to a complete eukaryotic genome. Both single-stranded and double-stranded DNAs are amplified efficiently. When the DNA fragments being amplified are less than one thousand bases, they can be very poor substrates for amplification unless they are circular. Amplification of the DNA molecule is such that the amount of amplified product is preferably at least about 10-fold amplified, more preferably the amplified product is 100-fold greater, or at least 1000-fold greater, or at least 10,000-fold greater, or at least 100,000-fold greater, or at least 1,000,000-fold greater, or at least 10,000,000-fold greater or even more than the DNA put into the reaction mixture. The constant temperature at which the amplification reaction is carried out is preferably less than 60° C., more preferably less than 45° C., and more preferably at 37° C.

In yet another preferred embodiment the reaction mixture contains ATP and CTP in addition to the 4 dNTPs.

A preferred source of the DNA molecule to be amplified is lysed E. coli cells and the DNA is either a plasmid, a bacterial artificial chromosome (BAC) or phage DNA. Preferably, the added plasmid DNA template is less than 100 ng and the reaction mixture is 10 to 200 µl.

The present method of amplification is especially useful to prepare a DNA molecule for use in a DNA sequencing reaction. Preferably, the reaction mixture containing the amplified DNA is treated with a phosphatase to remove dNTPs that may be present prior to use in a sequencing reaction. A preferred phosphatase is from arctic shrimp. The sequencing reaction preferably uses fluorescent primers or fluorescent dideoxynucleotides. A preferred embodiment for preparation of a DNA molecule for use in a sequencing reaction utilizes a polymerase in a reaction mixture such that the production of amplified product does not require exogenously-added oligonucleotide primers, the amplification is exponential, and the amount of amplified product is at least 10-fold greater than the amount of template DNA put into the mixture. More preferably the amplified product is 100-fold greater, or at least 1000-fold greater, or at least 10,000-fold greater, or at least 100,000-fold greater, or at least 1,000,000-fold greater, or at least 10,000,000-fold greater or even more than the DNA put into the reaction mixture.

In another embodiment, the invention features a method of isolating plasmid, phage, or bacterial artificial chromosomes (BAC) from bacterial cells, such as from E. coli cells and then amplifying that DNA in a reaction mixture that does not require exogenous oligonucleotide primers. The bacterial cells are lysed to form a lysate which is then added to the amplification reaction mixture. Lysis can be carried out by any method known to those who practice the art, such as the use of lysozyme or detergents. A preferred embodiment for amplifying DNA directly from a bacterial cell utilizes a polymerase in a reaction mixture such that the production of amplified product does not require exogenously-added oligonucleotide primers, the amplification is exponential, and the amount of amplified product is at least 10-fold greater than the amount of DNA in the lysate that was put into the reaction mixture. More preferably the amplified product is 100-fold greater, or at least 1000-fold greater, or at least 10,000-fold greater, or at least 100,000-fold greater, or at least 1,000,000-fold greater, or at least 10,000,000-fold greater or even more.

Other types of cells can also be used. In preferred embodiments, the cells are eukaryotic microbial cells, e.g., yeast cells, fungal cells or multi-nucleate structure, or mammalian cells, e.g., human cells.

In another embodiment the invention features a method of amplifying genomic DNA in order to preserve small amounts of DNA for the purposes of long-term storage. A preferred embodiment is the amplification of human genomic DNA from a small sample from a patient (e.g. a blood sample or cheek swab) that can then be used for genotype analysis.

In another embodiment the invention features a method of determining the amount of contaminating DNA in a sample by incubating the sample potentially containing contaminating DNA with a reaction mixture comprising a DNA polymerase such that if the contaminating DNA is present the DNA molecule is amplified to produce amplified product. At least one pre-determined amount of control DNA is incubated with the same reaction mixture to produce amplified control product. The amount of amplified product in the sample is compared with the amount of amplified control DNA as an indication of the amount of contaminating DNA in the sample. Alternatively, the rate of DNA synthesis is monitored in real-time using a probe that fluoresces only when bound to DNA; the greater the amount of input DNA, the shorter the lag period before the exponential phase of DNA synthesis can be observed (see Example 4).

Contaminating DNA refers to any DNA that may be contaminating a protein preparation. In general it is most likely to arise from the host organism in which the protein was obtained, and not purified adequately to remove it, or could be acquired during the purification of the protein from columns or reagents. Thus, the most likely source of contaminating DNA is E. coli, if the protein is a recombinant protein produced in E. coli, or it is human DNA if the protein is a recombinant protein produced in human tissue culture cells.

By "predetermined amount of control DNA" is meant an amount of DNA such as a supercoiled plasmid (e.g., pUC18 or pUC19) for example in the range of one femtogram to one nanogram in a 50 ul reaction. The synthesis obtained using this amount of DNA would be compared to an analogous reaction that was carried out in the absence of added DNA. The amount of synthesis at varying times specific for the added plasmid DNA would be determined by subtracting the amount of DNA synthesized in the absence of any DNA from that obtained in the presence of plasmid DNA. In further preferred embodiments the DNA polymerase is from bacteriophage T7, the reaction mixture further comprises a helicase, a primase and a single stranded binding protein, the control DNA is amplified at least about 10-fold, the reaction does not require exogenously-added oligonucleotide primers, the reaction mixture is carried out at a constant temperature, the control DNA is amplified at least 10-fold, and the kinetics of amplification of the control DNA is exponential.

In another aspect, the invention features a kit for amplification. The kit preferably contains a DNA polymerase, a primase, a helicase and a single-stranded binding protein. In further preferred embodiments, the components of the kit comprise those independently selected from the group consisting of a T7 DNA polymerase, the gene 4 protein from bacteriophage (the primase and the helicase), a DNA polymerase mixture of a wild-type T7 DNA polymerase and a T7 DNA polymerase modified to have reduced 3' to 5' exonuclease activity, and the single-stranded binding protein from E. coli. More preferably, these components, a T7 DNA polymerase, the gene 4 protein from bacteriophage (the primase and the helicase), a DNA polymerase mixture of a wild-type T7 DNA polymerase and a T7 DNA polymerase modified to have reduced 3' to 5' exonuclease activity, and the single-stranded binding protein from E. coli, are selected as a group. Still more preferably, the gene 4 protein is the 63-kDa form of the protein. The kit can also contain one or more of the following components: a nucleoside diphosphokinase, an inorganic pyrophosphatase, an ATP regeneration system, preferably consisting of phosphocreatine and creatine kinase, a T7 gene 6 exonuclease, a T7 DNA ligase (gene 1.3 protein) and a single-stranded DNA binding protein of bacteriophage T7 (gene 2.5 protein).

In a further aspect the invention features a method of purifying the T7 helicase/primase (63-kDa gene 4 protein) by overproducing the protein in an E. coli cell preferably along with a carboxy terminal fragment of the T7 gene 4 protein, preferably the peptide comprises the carboxy terminus of the protein after residue 221 (glutamine), more preferably the peptide comprises the carboxy terminus of the protein between residues 260 (tryptophan) and residue 280 (serine), even more preferably the peptide initiates at residue 271 (arginine). This gene 4 protein peptide reduces the toxicity of the full-length gene 4 protein to the cells and increases the expression level of the full-length gene by at least 10-fold.

In another embodiment the amplification reaction is carried out in a solid matrix such as agarose. Under these conditions, in the presence of a fluorescent dye such as SYBR Green II (Molecular Probes, Inc., Eugene, Oreg.) the amplification of single DNA molecules can be observed in a fluorescent microscope as focal centers of fluorescence that develop with time and are dependent on added DNA. In preferred embodiment, this amplification in a solid support is used to generate a library of individual "subclones" of DNA molecules, without having to passage the DNA through E. coli cells. More preferably these DNA clones are used as templates for DNA sequencing reactions, either by isolating individual clones and amplifying each in solution, or by carrying out the sequencing reaction using fluorescent dideoxy terminators on all the clones together simultaneously on the agarose support. This latter approach would allow a tremendous reduction in the amount (and thus the cost) of fluorescent sequencing reagents. Recently, Mitra and Church (*Nucleic Acids Research* 27:e34, 1999) have described a PCR-based system to amplify and detect individual DNA molecules embedded in a polyacrylamide support.

The invention also provides a method for sequencing a DNA sequence by providing amplified DNA, that has been amplified using the constant temperature amplification method described above. The resulting products are sequenced by any of the conventional methods, such as dideoxy termination methods, preferably in an automated sequencer. Preferably the amplification is carried out in a solid matrix, preferably a gel such as an agarose or polyacrylamide gel. Preferably a circular nucleic acid construct with primer sites suitable for extension through the sequence of interest is utilized, e.g., as described in Example 10. Thus, the invention provides an efficient method of sequencing nucleic acids.

As indicated above, the source of the template sequence to be amplified can be from any of a variety of sources, including, for example, nucleic acid molecules from blood from human or non-human, cheek swabs, other tissue samples, microbial cells such as bacterial cells, viruses, plasmids or other cloning vector sequences, or other purified sequences from any source including synthetic sequences.

Other features and advantages of the invention will be apparent from the following description of the preferred embodiments thereof and from the claims.

All articles, publications and patents cited in this application are hereby incorporated by reference, in their entirety.

BRIEF DESCRIPTION OF THE DRAWING

FIG. 1A-1C represents the nucleotide sequence of pGP4A/E-1 (SEQ. ID. NO. 1). Nucleotides 1-3 (ATG) correspond to the start codon for the 63-kDa gene 4 protein, while nucleotides 1699-1701 (TGA) correspond to its termination codon. Nucleotides 2785-2787 correspond to the start codon for the truncated gene 4 protein beginning at residue 271 (encoded for by the codon at nucleotides 2785-2787), while nucleotides 3670-3672 (TGA) correspond to the termination codon for this truncated gene.

DETAILED DESCRIPTION OF THE PREFERRED EMBODIMENTS

The following description and examples are provided for further illustrating various aspects and embodiments of the present invention and are in no way intended to be limiting in scope.

DNA Polymerase

In general a polymerase for use in this invention is one that carries out extensive DNA synthesis on both strands of a DNA template, with the synthesized DNA in turn being capable of being used as a template for new DNA synthesis. This results in an exponential increase in the amount of DNA synthesized with time. Many replicative DNA polymerases have accessory proteins such as processivity factors, helicases, primases and DNA binding proteins that are specific for each DNA polymerase (for review, see Kornberg and Baker, DNA Replication, Freeman and Co., New York, 1992). Many such combinations will result in efficient DNA synthesis. The bacteriophage T7 replication system provides one example of a polymerase and accessory proteins. Those of skill in the art will appreciate that combinations of polymerases and accessory proteins from other systems (e.g. bacteriophage T4 or E. coli) will also be useful in the present method of amplification. Such polymerases and accessory proteins can be used with all components being from one system, or can be used in other combinations with functionally compatible proteins from two or more different systems being utilized. Those of skill in the art would be able to determine such combinations of polymerases and accessory based on the Examples and descriptions provided.

In the T7 DNA replication system, a combination of two forms of the T7 DNA polymerase result in the most efficient DNA synthesis. One is the unmodified or native T7 DNA polymerase that has high 3' to 5' exonuclease activity (Tabor et al., *J. Biol. Chem.* 262:16212, 1987). The other is a form of T7 DNA polymerase that is deficient in its 3' to 5' exonuclease activity. An example of such a DNA polymerase is the Δ28 T7 DNA polymerase, missing residues from lysine 118 to arginine 145 (Tabor and Richardson, *J. Biol. Chem.* 264:6647, 1989; U.S. Pat. Nos. 4,942,130 and 4,946,786). Both these forms of T7 DNA polymerase have the processivity factor thioredoxin bound to them in a one-to-one complex. DNA synthesis is most efficient when the exonuclease-deficient form is in excess over native T7 DNA polymerase; the optimum molar ratio is about 20:1. Native and exonuclease deficient polymerases are known for other replication systems, such as bacteriophage T4, bacteriophage Ø29, and *E. coli* DNA polymerases I, II and III.

DNA Helicase

Most replicative DNA polymerases require a DNA helicase for strand displacement leading strand DNA synthesis. In each replication system the helicase interacts specifically with the DNA polymerase from that system. The energy for helicase activity is obtained by the hydrolysis of nucleoside triphosphates.

The helicase of bacteriophage T7 is the gene 4 protein. Its preferred substrate for hydrolysis is dTTP. The phage makes two forms of the gene 4 protein of molecular weight 56,000 and 63,000; the two forms arise from two in-frame start codons. Efficient amplification requires the 63-kDa form of the gene 4 protein, since, as discussed below, this form also provides primase activity (Bernstein and Richardson, *J. Biol. Chem.* 264:13066, 1989). Altered forms, substitutions, insertions, deletions, of the 63-kDa protein are also suitable for the present invention. One example is the 63-kDa gene 4 protein in which the methionine at residue 64 is changed to a glycine (G4A$_{G64}$). (Mendelman et al., *Proc. Natl. Acad. Sci. USA* 89:10638, 1992; Mendelman et al., *J. Biol. Chem.* 268:27208, 1993). This form of the 63-kDa gene 4 protein is useful because the mutation prevents the initiation of synthesis of the 56-kDa gene 4 protein. All enzymatic properties of the G4A$_{G64}$ form of the gene 4 protein that have been examined are comparable to those of the wild-type 63-kDa gene 4 protein, including its use as a primase and helicase for amplification as described in the current invention.

DNA Primase

In most replication systems, synthesis of the lagging strand is initiated from short oligoribonucleotide primers that are synthesized at specific sites by primases. Specific interactions between a primase and the DNA polymerase allow the DNA polymerase to initiate DNA synthesis from the oligoribonucleotide resulting in the synthesis of the lagging strand.

A unique primase mechanism is found in the terminal protein exemplified by adenovirus and bacteriophage Ø29 (Salas, *Ann. Rev. Biochem.* 60:39, 1991). In these organisms, duplex linear DNA is replicated by the covalent binding of the terminal protein to each 5' end, followed by initiation of DNA synthesis from a mononucleotide bound to the terminal protein by a DNA polymerase. While this system can provide a very efficient form of amplification of the phage genomes such as Ø29 DNA (Blanco et al., *Proc. Natl. Acad. Sci. USA* 91:12198, 1994), the nature of this priming mechanism makes it a difficult system to modify for general amplification of DNAs.

In the T7 replication system, the gene 4 protein, in addition to being a helicase, is also the primase (Bernstein and Richardson, *Proc. Natl. Acad. USA* 85:396, 1988; Bernstein and Richardson, *J. Biol. Chem.* 264:13066, 1989). Only the 63-kDa form of the gene 4 protein has primase activity. At specific pentanucleotide recognition sites, the 63-kDa gene 4 protein synthesizes tetraribonucleotides that are used as primers by T7 DNA polymerase to initiate lagging strand DNA synthesis. The synthesis of RNA primers by 63-kDa gene 4 protein requires ATP and CTP. However, the addition of exogenous short oligonucleotides (7 bases or less) can be used by the gene 4 protein to initiate DNA synthesis primers by T7 DNA polymerase (Scherzinger et al., *Nucleic Acids Research* 4:4151, 1977). The 63-kDa gene 4 protein is essential for amplification using the T7 replication system. While amplification is most efficient when ATP and CTP are present, it is possible that short oligonucleotides could be added to the reaction mixture to provide priming for amplification in the absence of ATP and CTP. While the native T7 DNA polymerase is capable of interacting with the 63-kDa gene 4 protein to initiate DNA synthesis from RNA primers, the Δ28 T7 DNA polymerase (missing residues 118 to 145) does so much less efficiently. This may be one explanation why a small amount of native T7 DNA polymerase is critical for efficient amplification.

Single-Stranded DNA Binding Protein

Most replication systems require single-stranded DNA binding proteins. They serve a number of roles (for review, see Kornberg and Baker, DNA Replication, Freeman and Co., New York, 1992). For example, they remove secondary structure from single-stranded DNA to allow efficient DNA synthesis.

The single-stranded DNA binding protein (ssb) from *E. coli* has been extensively characterized. It has a dramatic effect on improving the processivity of T7 DNA polymerase, particularly at temperatures below 30° C. (Tabor et al., *J. Biol. Chem.* 262:16212, 1987). A low level of ssb is required for efficient amplification using the T7 replication proteins described in this invention. Optimally, the amount of ssb for a 50 μl reaction is from 0.01 to 1 μg.

Bacteriophage T7 also encodes its own single-stranded DNA binding protein, the gene 2.5 protein (Kim et al., *J. Biol. Chem.* 267:15022, 1992) The presence of this protein is less important for amplification than is the *E. coli* single-stranded DNA binding protein. However, it does stimulate the rate of DNA synthesis several-fold at a concentration of from 0.05 to 5 μg in a 50 μl reaction containing the core amplification components.

Nucleoside Diphosphokinase

Nucleoside diphosphokinase rapidly transfers the terminal phosphate from a nucleoside triphosphate to a nucleoside diphosphate. It is relatively nonspecific for the nucleoside, recognizing all four ribo- and deoxyribonucleosides. Thus it efficiently equilibrates the ratio of nucleoside diphosphates and nucleoside triphosphates among all the nucleotides in the mixture. This enzyme can increase the amount of DNA synthesis if one of the required nucleoside triphosphates is preferentially hydrolyzed during the reaction.

In the bacteriophage T7 replication system, the T7 helicase (gene 4 protein) hydrolyzes dTTP to dTDP to provide energy (Matson and Richardson, *J. Biol. Chem.* 258:14009, 1983). Thus the concentration of dTTP will decrease disproportionately during DNA synthesis. The addition of nucleoside diphosphokinase will re-equilibrate the level of triphosphates of all the nucleosides present. This results in an increase of several-fold in the amount of DNA synthesized. Nucleoside diphosphokinase from Baker's Yeast can be purchased from Sigma Chemical Co. (St. Louis, Mo.) and the overproduction and purification of nucleoside diphosphokinase from *E. coli* has been described (Almaula et al. *J. Bact.* 177:2524, 1995). Other nucleoside diphosphokinases are known to those who practice the art and are useful in the present invention.

Inorganic Pyrophosphatase

During a DNA synthesis reaction, inorganic pyrophosphate will accumulate as a product of the reaction. If the concentration becomes too high, it can reduce the amount of DNA synthesis due to product inhibition. This can be prevented by the addition of inorganic pyrophosphatase. Yeast inorganic pyrophosphatase can be purchased from Sigma Chemical Co. (St. Louis, Mo.). Other inorganic pyrophosphatases are known to those who practice the art and are useful in the present invention.

ATP-Regenerating System

During DNA synthesis in many DNA replication systems, some of the deoxynucleoside triphosphates will be degraded to deoxynucleoside diphosphates due to hydrolysis by the helicase present. This can be minimized by the use of an ATP regeneration system which, in the presence of nucleoside diphosphokinase, will convert any nucleoside diphosphate in the reaction mixture to the triphosphate. In the T7 replication system, the helicase very rapidly degrades dTTP to dTDP for energy. The presence of an ATP-regeneration system will increase the amount of nucleotides capable of serving as precursors for DNA synthesis.

A number of ATP regeneration systems are available and have been widely used. For example, the combination of phosphocreatine and creatine kinase will push the equilibrium between ADP and ATP towards ATP, at the expense of the phosphocreatine. Both phosphocreatine and creatine kinase are available from Sigma Chemical Co. (St. Louis, Mo.).

Joining Lagging Strand Fragments

In most DNA replication systems, the lagging strand is synthesized as a series of short, "Okazaki" fragments, that are initiated by a short RNA primer at each 5' end. In order to form a continuous strand, a 5' to 3' exonuclease is needed to remove the RNA primer, and then, after a DNA polymerase fills in the gap, a DNA ligase is needed to seal the nick. In the T7 DNA replication system, these functions are accomplished by the action of the gene 6 protein, a 5' to 3' exonuclease, and the gene 1.3 protein, a DNA ligase (Engler and Richardson, *J. Biol. Chem.* 258:11197, 1983). Purification of the gene 6 protein (Kerr and Sadowski, *J. Biol. Chem.* 247:305, 1972; Engler and Richardson, *J. Biol. Chem.* 258:11197, 1983) and gene 1.3 protein (Doherty et al., *J. Biol. Chem.* 271:11083, 1996) have been described. Exonucleases and ligases from other replication systems are known to those who practice the art and are useful in the present invention.

Removal of Contaminating DNA from Enzymes

Since the amplification system described in this invention is nonspecific, contaminating DNA will potentially be a serious source of background. This is particularly a problem in enzyme preparations in which the enzymes bind DNA, such as DNA polymerases, helicases and DNA binding proteins. Most DNA can be removed from enzyme preparations during purification. For example, an anion exchange column such as DEAE will bind DNA much tighter than it binds proteins.

The residual DNA present in enzyme preparations can be inactivated as a template for DNA synthesis by treatment of the enzymes with ultraviolet light. Effective doses of ultraviolet light are 10 to 1000 $\mu W/cm^2$. In the T7 replication system, treatment of the enzymes with an ultraviolet dose of 200 $\mu W/cm^2$ for 2 min reduces the background synthesis due to contaminating DNA by 99%, while it reduces the activity of the enzymes by less than 20%. This dose of ultraviolet light is equivalent to the dose obtained using a standard, hand-held short-wave ultraviolet light source 10 cm from the enzyme mixture. The enzyme mixture is kept on ice during the treatment with ultraviolet light to help maintain its activity.

Removal of Unincorporated Nucleoside Triphosphates from Reaction Mixture

In order to be used for DNA sequencing reactions, the template DNA added to the reactions can only have low levels of unincorporated dNTPs. An efficient method of removing dNTPs is to treat the amplified product with alkaline phosphatase such as that from arctic shrimp (Amersham Pharmacia Biotech, Inc., Piscataway, N.J.). This phosphatase is rapidly inactivated by treatment at elevated temperatures. Thus treatment of a 50 $\mu l$ reaction mixture with 0.1 to 10 units of shrimp alkaline phosphatase at 20-37° C. for 10 to 60 min, followed by treatment at 65-95° C. for 10 to 60 min, results in template DNA free of dNTPs that can be added directly to a DNA sequencing reaction such as the dye terminator reactions using AmpliTaq FS enzyme (Applied Biosystems, Foster City, Calif.) or ThermoSequenase enzyme (Amersham Pharmacia Biotech Inc., Piscataway, N.J).

Reaction Mixture for Amplification Using T7 Replication Proteins

Reaction mixtures contain a buffer at a concentration of 5 mM to 50 mM at pH 7.0 to 8.5, preferably pH 7.5; e.g., 20-40 mM Tris-glutamate, pH 7.5. 2 mM to 15 mM $Mg^{2+}$ is required, preferably 5 to 10 mM; e.g., 9 mM $MgCl_2$. A reducing agent is present, such as 1 to 50 mM dithiothreitol or 2-mercaptoethanol; e.g. 5 mM dithiothreitol. The reaction mixture contains 50 to 200 mM potassium glutamate; e.g. 100 mM potassium glutamate, which stimulates the reaction. In contrast chloride salts generally inhibit the reaction; if NaCl or KCl are present, preferably their concentration is below 50 mM. The 4 dNTPs are present at a concentration preferably between 20 and 2,000 $\mu M$, most preferably at a concentration of 500-1000 $\mu M$ of each dNTP. rATP and rCTP are each present at a concentration between 20 and 2000 $\mu m$, most preferably at a concentration of 500 to 1000 $\mu M$. Other chemicals may be added that enhance the amplification reaction. For example, DMSO between 0.5 and 8% gives an increased amount of DNA synthesis, most preferably a concentration of 4%. Similarly, a dextran such as Dextran T-10 or Dextran T-500 polysaccharide (Amersham Pharmacia Biotech. Inc., Piscataway, N.J.) between 0.5 and 20% enhances the amount of DNA synthesis, most preferably a concentration of 5%. After the addition of the DNA to be amplified and the enzyme mixture containing at least some of the T7 replication enzymes described above, the reaction is allowed to proceed at a temperature between 10° C. and 50° C., preferably 37° C., for 10 to 60 min, preferably 20 min. The reaction can be stopped using standard procedures such as the addition of EDTA to a final concentration of 25 mM, or heating the mixture at 70° C. for 20 minutes.

Sequencing from Single Molecule Amplification

The amplification reaction can be used to provide DNA for sequencing. The amplification is carried out in a solid matrix such as agarose. Under these conditions, in the presence of a fluorescent dye such as SYBR Green II (Molecular Probes, Inc., Eugene, Oreg.) the amplification of single DNA molecules can be observed in a fluorescent microscope as focal centers of fluorescence that develop with time and are dependent on added DNA. Low-melt agarose such as SeaPlaque Agarose (FMC Products, Rockland, Me.) is preferred as the matrix, since the DNA can be easily removed from the agarose when desired by heat. It may be helpful to use a combination of agaroses or other matrices to optimize the stability of the individual foci in the solid support while allowing the DNA to be readily extracted when desired.

If the single molecules being amplified are from a large DNA fragment that has been digested with a restriction enzyme (e.g. EcoRI), and then ligated intramolecularly to form circular molecules, the collection of foci within the agarose support will correspond to a population of "subclones" of that original DNA molecule, comparable to subclones obtained more conventionally by transforming these molecules into *E. coli* and then plating the cells to obtain individual clones. The advantage of the approach described here is that the entire library of clones is generated without the need to transform the DNA into bacteria, and that each "clone" observed as a foci in agarose is pure DNA that can be used directly for sequencing or other applications. Recently, Mitra and Church (Nucleic Acids Research 27:e34, 1999) have described a PCR-based system to amplify and detect individual DNA molecules embedded in a polyacrylamide support.

Several different approaches can be used to sequence the DNA amplified in the agarose support. One would be to pick the DNA from each foci into a tube, heat at 70° C. to melt the agarose, and then add an aliquot to a new amplification reaction mixture to amplify the DNA in solution. This amplified DNA could then be used for DNA sequence analysis as described in Example 5.

Alternatively, the DNA on the agarose support could be sequenced directly. The unincorporated nucleotides from the amplification would first be removed by soaking the agarose in a suitable buffer, e.g., 10 mM Tris-HCl, pH 7.5, 1 mM EDTA. The DNA in the agarose would then be denatured by treatment with 10 mM NaOH for 5 min, followed by neutralization by several washes in 10 mM Tris-HCl, pH 7.5, 1 mM EDTA. The primer used for DNA sequencing would then be soaked into the agarose and allowed to anneal to the denatured DNA. Excess primer would be removed by several washes in 10 mM Tris-HCl, pH 7.5, 1 mM EDTA, and then the DNA sequencing reactions would be carried out by the addition of sequencing reaction buffer, fluorescent nucleotides (e.g. BigDye nucleotides from PE Biosystems (Foster City, Calif.)), and a DNA polymerase such as AmpliTaq FS (PE Biosystems, Foster City, Calif.). The reaction would be initiated by heating the sample to 70° C. After a 10 min reaction, the sample would be chilled to 4° C., and the product DNA would be denatured by treatment again with 10 mM NaOH for 5 min. Finally, the salt would be removed by extensive washing in water.

The samples are now ready to be directly loaded onto a capillary DNA sequencing instrument. Injection of the capillaries would be a modification of that used in existing instruments such as the PEBiosystems 3700 Genetic Analyzer (Foster City, Calif.). One direct-load approach would be to insert a 100-1000 capillary array into the sample, heat to 70° C. to melt the agarose, and then apply a voltage to electrosmotically inject the DNA into each capillary. While only a subset of the capillaries would contain DNA from a single foci, and thus produce unique DNA sequence, the advantages of this procedure would be the ease of carrying out multiple sequencing reactions simultaneously and the low reagent cost of carrying out such parallel reactions.

EXAMPLE 1

Amplification of Purified Plasmid DNA Using a Minimal Number of T7 Replication Proteins The reaction mixture (45 µl) contains 20 mM Tris-glutamate, pH 7.5, 9 mM $MgCl_2$, 6 mM dithiothreitol, 100 mM potassium glutamate, 3.5% dimethylsulfoxide (DMSO), 7% Dextran T-500 polysaccharide (Amersham Pharmacia Biotech, Inc., Piscataway, N.J.), 550 µM each dGTP, dATP, dTTP and dCTP, 330 µM ATP, 440 µM CTP, and DNA. The DNA samples range from 0.1 pg to 10 ng of supercoiled double-stranded plasmid DNA.

Although circular DNA is a preferred substrate for amplification, linear DNA can also be used. The DNA can be either single- or double-stranded. In addition to plasmid DNA, other DNAs such as phage lambda DNA, phage M13 DNA bacterial artificial chromosomal (BAC) DNA and genomic DNA (e.g., bacterial or human) are effective templates for amplification. Synthetic DNA such as oligonucleotides 100 nucleotides in length can be used if they are first ligated to form circular molecules. Data suggest that for cicular DNA molecules the initial stages of amplification involve a rolling circle mechanism.

One method of initiating rolling circle DNA synthesis on a plasmid DNA from a specific site that has been described is to use the site-specific single-stranded endonuclease gene II protein from filamentous phage such as M13 or fd. This protein recognizes a sequence of approximately 50 bp (the plus strand replication origin) and introduces a specific nick into one of the strands (Higashitani et al., *Nucleic Acids Research* 20:2685, 1992). While the wild-type gene II protein requires supercoiled DNA for activity, mutant proteins have been described (e.g. glycine 73 changed to alanine) that reduce this superhelicity requirement, so that the protein now recognizes relaxed duplex DNA (Higashitani et al., *Nucleic Acids Research* 20:2685, 1992). The purification of the wild-type and mutant gene II proteins have been described (Greenstein and Horiuchi, *J. Molec. Biol.* 197:157, 1987; Higashitani et al., *Nucleic Acids Research* 20:2685, 1992). It has been demonstrated that cleavage of supercoiled DNA with the gene II protein results in a substrate that the T7 DNA polymerase and T7 gene 4 protein can use to initiate lagging strand DNA synthesis (Harth et al., *Eur. J. Biochem.* 119:663, 1981). It has also been demonstrated that these molecules promote rolling circle DNA synthesis using the replication proteins from bacteriophage T4 (Meyer et al., *J. Biol. Chem.* 256:5810, 1981). This class of site-specific nicking proteins may be useful for stimulating initiation of the amplification process described in this invention. However, in the invention described here the inventors have shown that surprisingly nicking of the circular DNA is not necessary for efficient initiation of DNA synthesis; the combination of T7 gene 4 protein and T7 DNA polymerase are able to efficiently initiate and synthesize DNA on covalently supercoiled plasmid DNAs whether they are supercoiled or relaxed.

For diagnostic characterization of the extent of DNA synthesis, one of the dNTPs can be radioactively labeled; for example, [$^3$H] dTTP can be used at a specific activity of 20 cpm/pmol. The synthesized DNA can also be detected by fluorescence or chemiluminescence by incorporating the appropriate modified nucleotides using standard techniques (Current Protocols in Molecular Biology, Ausubel et al., eds., John Wiley & Sons, Inc., 1996).). In addition, the rate of DNA synthesis can be monitored in real time by the addition of a fluorescent probe to the reaction mixture (see Example 4).

The enzyme mixture (5 μl per reaction) is prepared in a buffer containing 20 mM Tris-glutamate, pH 7.5, 10 mM 2-mercaptoethanol and 0.5 mg/ml bovine serum albumin. 5 μl of this mixture contains 1 μg of Δ28 T7 DNA polymerase, 0.03 μg of native T7 DNA polymerase, 1 μg of T7 63-kDa gene 4 protein, and 0.3 μg of *E. coli* single-stranded DNA binding protein. Δ28 T7 DNA polymerase is a one-to-one mixture of *E. coli* thioredoxin and T7 gene 5 protein with a deletion of residues 118 to 145, as described in Tabor and Richardson, *J. Biol. Chem.* 264:6647, 1989, and U.S. Pat. Nos. 4,942,130 and 4,946,786. It is the same as Sequenase Version 2.0 enzyme sold by Amersham Pharmacia Biotech, Inc. (Piscataway, N.J.). Native T7 DNA polymerase is a one-to-one complex of thioredoxin and wild-type T7 gene 5 protein. It can be purchased from Amersham Pharmacia Biotech, Inc. (Piscataway, N.J.) or New England Biolabs (Beverly, Mass.). T7 63-kDa gene 4 protein is the G4A$_{G64}$ protein described in Mendelman et al., *Proc. Natl. Acad. Sci. USA* 89:10638, 1992 and Mendelman et al., *J. Biol. Chem.* 268: 27208, 1993; it is the wild-type gene 4 63 kDa protein except that the methionine at residue 64 has been replaced with a glycine to prevent initiation of synthesis of the 56-kDa form of the gene 4 protein. *E. coli* single-stranded DNA binding protein (ssb) is overproduced and purified as described in Lohman et al., *Biochemistry* 25:21 (1986). It can be purchased from Amersham Pharmacia Biotech, Inc. (Piscataway, N.J.).

In order to reduce the level of background DNA synthesis resulting from contaminating DNA, the enzyme mixture is treated with ultraviolet light at a dose of 200 μW/cm$^2$ for 2 min on ice prior to adding to the reaction mixture. This dose corresponds to a distance of about 10 cm from a standard short-wave ultraviolet lamp. Times of 10 sec to 15 min are also effective at reducing the amount of contaminating DNA that can be replicated without affecting significantly the activity of the enzymes.

To initiate the amplification reaction, 5 μl of the enzyme mixture is added to the 45 μl reaction mixture. The reaction is then allowed to proceed at 37° C. for 20 min. The reaction can be carried out at a temperature of 10° C. to 45° C., for 1 min to 2 hr. The reaction is stopped by the addition of 5 μl of 200 mM EDTA.

There are many published procedures to measure the amount of DNA synthesized during the reaction. For example, if [$^3$H]dTTP is present, the amount of radioactivity incorporated into DNA can be measured by binding the reaction mixture to a DE81 filter disk, then washing the disk with 0.3 M ammonium formate to remove unincorporated nucleotides, and then measuring the amount of radioactivity retained on the disk using a scintillation counter, as described in Kim et al., *J. Biol. Chem.* 267:15032 (1992). Alternatively, the DNA can be analyzed by agarose gel electrophoresis and staining with ethidium bromide, either with or without digestion with restriction enzymes, following standard procedures (Current Protocols in Molecular Biology, Ausubel et al., eds., John Wiley & Sons, Inc., 1996).

This procedure should result in the incorporation of about 5% of the total dNTPs into DNA, or about 1.5 μg of DNA synthesized in the 50 μl reaction mixture. If the reaction mixture contains 10 pg of plasmid DNA, this corresponds to a 150,000-fold amplification.

EXAMPLE 2

Amplification of Purified Plasmid DNA Using a T7 Replication System Optimized for Maximum Rate and Amount of DNA Synthesis The rate and amount of DNA synthesis obtained using the conditions defined in Example 1 can be improved by using the modifications described below. All other components and conditions are identical to those outlined in Example 1.

Phosphocreatine (11 mM) is added to the 45 μl reaction mixture. This in combination with creatine kinase provides an efficient ATP regeneration system. The phosphocreatine that is most effective is synthetic phosphocreatine, Sigma catalog number P6502 (Sigma Chemical Co., St. Louis, Mo.), dissolved in H$_2$O to a concentration of 500 mM.

The enzyme mixture contains at least some of the following six enzymes. These are in addition to the Δ28 T7 DNA polymerase, native T7 DNA polymerase, 63-kDa gene 4 protein and *E. coli* single-stranded DNA binding protein, which are present in the amounts defined in Example 1.

(1) Creatine kinase, rabbit muscle (Boehringer catalog number 127566) (Boehringer Mannheim, Indianapolis, Ind.). A stock solution is prepared at 100 mg/ml in H$_2$O and stored at −40° C. Each enzyme mixture (5 μl) for a 1× reaction (50 μl total volume) contains 2 μg of creatine kinase. Creatine kinase, in conjunction with phosphocreatine and nucleoside diphosphokinase, provides an ATP regeneration system that converts nucleoside diphosphates that arise during the reaction to nucleoside triphosphates.

(2) Nucleoside diphosphokinase, Baker's yeast (Sigma catalog number N0379) (Sigma Chemical Co., St. Louis, Mo.). A stock solution is prepared at 1 mg/ml in H$_2$O and stored at −40° C. Each enzyme mixture (5 μl) for a 1× reaction (50 μl total volume) contains 50 ng of nucleoside diphosphokinase. Alternatively, nucleoside diphosphokinase can be overproduced and purified from *E. coli* (Almaula et al., *J. Bact.* 177:2524, 1995). 50 ng of the *E. coli* enzyme is used for a 1× reaction. Nucleoside diphosphokinase is added to maintain an equal ratio of all four dNTPs.

(3) Inorganic pyrophosphatase, Baker's yeast (Sigma catalog number I1891) (Sigma Chemical Co., St. Louis, Mo.). A stock solution is prepared at 1 mg/ml in H$_2$O and stored at −40° C. Each enzyme mixture (5 μl) for a 1× reaction (50 μl total volume) contains 20 ng of inorganic pyrophosphatase. Inorganic pyrophosphatase is added to degrade the pyrophosphate that will build up during polymerization and could inhibit DNA synthesis by product inhibition.

(4) T7 single-stranded DNA binding protein (T7 gene 2.5 protein). T7 single-stranded DNA binding protein is overproduced and purified as described by Kim et al. (*J. Biol. Chem.*, 267:15022, 1992). Each enzyme mixture (5 μl) for a 1× reaction (50 μl total volume) contains 1 μg of T7 single-stranded DNA binding protein. The T7 single-stranded DNA binding protein will increase the rate of DNA synthesis by several-fold. One possible explanation for this is that the T7 single-stranded DNA binding protein is necessary to have efficient coupling of leading and lagging strand DNA synthesis by the T7 DNA polymerase and helicase/primase complex (Park et al., *J. Biol. Chem.* 273:5260, 1998; Lee et al., *Mol. Cell.* 1:1001, 1998).

(5) T7 gene 6 exonuclease. The combination of T7 gene 6 exonuclease and T7 DNA ligase (T7 gene 1.3 protein) are used to remove the RNA primers from the 5' ends of the lagging strand fragments and then, after the gaps are filled in by the wild-type T7 DNA polymerase, seal the resulting nicks. The T7 gene 6 exonuclease is purified as described in Kerr and Sadowski, *J. Biol. Chem.* 247:305, 1972 and Engler and Richardson, *J. Biol. Chem.* 258:11197, 1983. Each enzyme mixture (5 µl) for a 1× reaction (50 µl total volume) contains 50 ng of T7 gene 6 exonuclease.

(6) T7 DNA ligase (gene 1.3 protein). The T7 ligase is added to seal any nicks that are present in the synthesized DNA, in particular those that occur on the lagging strand. T7 DNA ligase is overproduced and purified as described in Doherty et al., *J. Biol. Chem.* 271:11083, 1996. Each enzyme mixture (5 µl) for a 1× reaction (50 µl total volume) contains 0.1 µg of T7 DNA ligase.

As in Example 1, the enzyme mixture is treated with an ultraviolet dose of 200 µW/cm$^2$ for 2 min on ice prior to adding to the reaction mixture. The amplification reaction is then initiated by the addition of 5 µl of the enzyme mixture to the 45 µl reaction mixture. The reaction is allowed to proceed at 37° C. for 20 min, and then stopped by the addition of 5 µl of 200 mM EDTA. The products are analyzed as described in Example 1.

This procedure should result in the incorporation of up to 50% of the total dNTPs into DNA, or about 15 µg of DNA synthesized in the 50 µl reaction mixture. If the initial reaction mixture contains 10 pg of plasmid DNA, this corresponds to a 1,500,000-fold amplification.

EXAMPLE 3

Assay to Determine Whether Amplification is Exponential

Reactions as described in Examples 1 and 2 are carried out using varying amounts of plasmid DNA and for varying lengths of time. A radioactively labeled dNTP is used in order to determine the amount of DNA synthesis; for example, 50 cpm/pmole [$^3$H]dTTP or [α-$^{32}$P]dATP. 100 µl reactions are carried out in the absence of added DNA, and in the presence of 1, 10, 100 and 1,000 pg of supercoiled pUC18 plasmid DNA. Reactions are carried out at 37° C. and 20 µl aliquots are removed at 5, 10, 15, 20 and 30 min and stopped by the addition of 5 µl of 200 mM EDTA, pH 8.0. The amount of radioactivity incorporated into DNA is determined using standard methods. For example, the amount of radioactivity that can be precipitated by trichloracetic acid, which will precipitate DNA but not free nucleotide, can be determined as described in Tabor and Richardson, *J. Biol. Chem.* 264:6647, 1989. Alternatively, the amount of radioactivity that is retained by DE81 filter disks in the presence of 0.3 M ammonium formate, pH 8.0, can be determined (Kim et al., *J. Biol. Chem.* 267:15032, 1992); DNA but not dNTPs is retained by the disks under these conditions.

For each time point, the amount of DNA synthesized in the absence of added DNA is subtracted from the amount synthesized in the presence of DNA. Up to 20 min, the amount of DNA synthesized in the absence of added input DNA should be very low (for example, less than 1% the amount synthesized in the presence of 100 pg of added input DNA).

For each amount of input DNA, the amount of DNA synthesized above the background level synthesized in the absence of input DNA is plotted as a function of the time of the reaction. If amplification is exponential, then the rate of synthesis of DNA will increase during some portion of the time course (i.e., the plot will be sigmoidal). For example, the amount of DNA synthesized after 15 min might be 50-fold higher than the amount synthesized after 10 min.

EXAMPLE 4

Real-Time Amplification Assay Using Fluorescence

A very effective method of monitoring the amount of DNA synthesized using the isothermal exponential amplification system is to use fluorescent probes to continuously report the amount of DNA in the reaction in real time. The basic principle of this method has been used successfully to determine the initial concentrations of specific RNAs and DNAs in a PCR reaction (Gibson et al., *Genome Research* 6:995, 1996). The higher the initial DNA concentration, the shorter the lag period before the exponential phase of DNA synthesis. To measure the amount of DNA synthesis in real time, reactions were carried out as described in Example 3 except that radioactivity was omitted and the fluorescent dye SYBR Green II (Molecular Probes, Eugene, Oreg.) was added at a final concentration of 1/80,000 the stock solution. The dye was added after the reaction mixture was treated with UV light to destroy contaminating DNA. SYBR Green II has virtually no fluorescence on its own but fluoresces very strongly when bound to nucleic acid. At concentrations higher than 1/80,000 of the initial stock it is inhibitory to the amplification reaction described in Example 3. Other dyes that fluoresce specifically when bound to nucleic acid will also work in the present invention (e.g. SYBR Green I, Pico Green, Oligreen, SYTO 11, SYTO 12, SYTO 13, SYTO 14, SYTO 15, SYTO 16 (Molecular Probes, Eugene, Oreg.), and SYBR Green (PE Biosystems, Foster City, Calif.)) or any other dye which shows significantly enhanced fluorescence when bound to DNA. Preferably, the significantly enhanced fluorescence refers to at least a 10-fold increase in fluorescence upon binding to DNA. More preferably, DNA binding will result in at least a 30-fold, 100-fold, 300-fold or 1000-fold increase in fluorescence.

In the example, reactions are carried out at 37° C. Fluorescence is monitored once every 15 sec for 30 min. Exemplary instruments that can be used to measure fluorescence include real-time PCR instruments such as the PE Biosystems 5700 (PE Biosystems, Foster City, Calif.) and the Roche LightCycler (Indianapolis, Ind.), and fluorescence microtiter plate readers that can maintain a constant temperature and can carry out kinetic measurements, such as the SPECTRAmax (Molecular Devices, Sunnyvale, Calif.). Ideally the SYBR Green II fluorescence is monitored using an excitation wavelength of 480 nM and an emission wavelength of 530 nM.

In order to measure the DNA concentration in unknown samples, a standard curve is determined for each experiment by carrying out reactions either in the absence of DNA (blank) or in the presence of known concentrations of a standard DNA such as supercoiled pUC18 (e.g. ten-fold dilutions from 0.1 pg to 10 ng). A standard curve is determined by plotting the time required for fluorescence to reach half-maximum (or alternatively the time required for the relative fluorescence to reach some threshold value) versus the log of the initial concentration of DNA. This plot yields a straight line over at least three orders of magnitude of initial DNA concentration. A comparison of the values obtained using unknown samples to the standard curve allows one to extrapolate the amount of DNA present at the outset in each sample.

EXAMPLE 5

Use of Amplified DNA as a Template for DNA Sequencing Reactions

The following example shows how the amplification reaction can be used to generate enough template from a small amount of DNA to be sequenced using conventional radioactive and nonradioactive dideoxy terminator sequencing strategies. While the example shown is starting from a small amount of plasmid DNA, this procedure will also work using other DNAs such as those from bacterial artificial chromosomes (BACs), phage lambda, phage M13, or genomic DNA (e.g., bacterial or human). Also, while the example shown uses purified DNA, much less pure samples, such as that from freshly lysed E. coli cells, can also be used.

Supercoiled pUC18 DNA (100 pg) is added to a 50 µl reaction mixture as described in Example 2, and amplified at 37° C. for 20 min. The reaction is stopped by heating the mixture at 70° C. for 5 min. 0.5 units of arctic shrimp alkaline phosphatase (Amersham catalog number E70092) (Amersham Pharmacia Biotech, Inc., Piscataway, N.J.) is added, and the mixture is incubated at 37° C. for 30 min. The phosphatase is then inactivated by incubation at 80° C. for 15 min. The amplified DNA can now be directly added to a DNA sequencing reaction. Other methods can also be used to purify the template DNA away from unincorporated dNTPs. These include precipitating the DNA with ethanol or isopropanol, and purifying the DNA by binding it to a silica matrix, for example using a commercial kit such as the QIAquick PCR Purification Kit, product number 28104. (Qiagen, Inc., Valencia, Calif.).

In order to sequence the amplified DNA using the PE Biosystems BigDye Terminators (catalog number 4303149 (PE Biosystems, Foster City, Calif.), 1 µl of the amplified DNA (500 ng) that had been treated with arctic shrimp phosphatase was added to 8 µl of the BigDye Reaction Mixture, 1.5 µl (3 pmoles) of the "universal" forward primer, and 9.5 µl of water. Cycle sequencing was carried out using 25 cycles consisting of 96° C. for 10 sec, 50° C. for 5 sec, and then 60° C. for 4 min. After the reaction was complete the unincorporated dye terminators were removed by gel filtration centrifugation using Centri-Sep columns (Princeton Separations, Inc., Princeton, N.J.) and the eluent was used directly for capillary sequence analysis on the PE Biosystems 310 single-capillary Genetic Analyzer or the PE Biosystems 3700 96-capillary Genetic Analyzer. The accuracy of the sequence was analyzed by determining the number of bases that had a Phred score greater than 20 (Ewing et al., *Genome Research* 8:186, 1998). In general, three times less amplified DNA was required compared with supercoiled plasmid DNA to produce DNA sequence of a given quality as analyzed by their relative Phred scores. This is probably due to the fact that primers will anneal more efficiently to the amplified DNA since it is linear compared with the supercoiled plasmid DNA.

The amplified DNA can also be sequenced using other methods of labeling the fragments. For example, it can be used a template for reactions containing radioactively labeled dideoxyterminators; 2 µl of the DNA can be added directly to the 20 µl reaction mixture from a ThermoSequenase radiolabeled terminator cycle sequencing kit, Amersham Pharmacia product number US 79750 (Amersham Pharmacia Biotech, Inc., Piscataway, N.J.). The DNA can also be used for DNA sequencing techniques that use either radioactive or fluorescently labeled primers.

EXAMPLE 6

Amplification and Sequencing of Plasmid DNA Directly from a Bacterial Colony

The procedure below describes the amplification in vitro of DNA obtained from direct lysis of a bacterial colony, followed by DNA sequencing of the amplified DNA. While the example is using cells containing a high copy plasmid (pUC18), one skilled in the art will recognize that cells containing other types of DNAs, such as bacterial artificial chromosome (BAC) DNAs, could also be used in this procedure.

Bacterial cells containing the plasmid to be amplified and sequenced, for example a pUC18 derivative, are plated on LB plates containing 50 µg/ml ampicillin at 37° C. overnight. A single colony is placed in 500 µl of a solution containing 20 mM Tris-HCl, pH 7.5, 1 mM EDTA and 100 µg lysozyme. After incubation at room temperature for 15 min, the solution is centrifuged at 14,000 rpm for 10 min. 1 µl of the supernatant is then added to a 50 µl amplification reaction as described in Example 2. The resulting amplified DNA is then sequenced as described in Example 4. While the centrifugation step removes genomic DNA and thus improves the purity of the sample, it is possible to avoid this step and use the lysed sample directly for amplification and sequencing.

While the lysis method described here uses lysozyme, other methods could be used, such as the addition of nonionic detergents (e.g. Triton X-100 or Tween 20) or the expression of the T7 lysozyme gene (gene 3.5 protein) within the E. coli cell (pLysS and pLysE, Novagen, Inc., Madison, Wis.). It is possible that the method of lysis will have to be optimized for plasmids of varying size in order to minimize the amount of contaminating chromosomal DNA released.

EXAMPLE 7

BAC End Sequencing by Selective Amplification of the Ends of the Insert

In this example the ends of BAC clones are sequenced by first preferentially amplifying DNA fragments containing the ends of each insert. This is accomplished by digesting the BAC DNA and then carrying out a ligation in the presence of a splint that will result in circularization of only the two end fragments. Since the amplification system described in Example 2 preferentially amplifies circular DNA when the DNA fragments are less than several kbp, this circularization results in an enrichment of the end fragments in the final amplified mixture. (This is not necessarily the case for other amplification systems of the invention.) While the example below uses the vector pBELO-11 (Research Genetics, Huntsville, Ala.), which has a single Bae I site and no Mlu I sites, the strategy used can readily be applied to other BAC vectors by choosing the appropriate restriction enzymes and designing the appropriate splint oligonucleotides.

pBELO-11 BAC DNA containing inserts is isolated from E. coli cells using standard procedures. 50 ng of the DNA is treated with the enzymes Bae I, Mlu I and T4 DNA ligase (New England Biolabs, Beverly, MA) and a 50-fold molar excess of the following three oligonucleotides: BAC-1 (5'-CGCGGTACACCGACGTCAA-3') (SEQ ID NO: 2), BAC-2 (5'-CGCGGTACACCGACTTAAT-3') (SEQ ID NO: 3) and BAC-3 (5'-GTCGGTGTAC-3') (SEQ ID NO 4). BAC-1 and BAC-3 will anneal to form a split that will result in circularization and ligation of one end of the pBELO-11 DNA, while BAC-2 and BAC-3 will anneal to form a split that will result in circularization and ligation of the other end of the pBELO-11 DNA. The reactions are carried out in 20 µl in 20 mM Tris-HC1, pH 7.5, 10 mM MgCl$_2$, 5 rnM DTT, 20 µM S-adenosylmethionine and 500 µM ATP at 37° C. for 60 min. 5 µl of the ligated products are amplified as described in Example 2 in a 50 µl reaction. After removal of the unincorporated nucleotides, the amplified DNA is sequenced using the universal T7 (TAATACGACTCACTATAGGGCGA) (SEQ ID NO: 5) or SP6 (CATACGATTTAGGTGACACTATAG) (SEQ ID NO: 6) primers that anneal upstream of each of the two ends of the insert in pBELO-11

EXAMPLE 8

Generic Amplification of Human Genomic DNA

A cheek swab is taken of a human subject and applied to FTA Card (GIBCO BRL, Rockville, Md.). The DNA bound to the paper is purified using FTA Purification Reagent as described by the distributor (GIBCO BRL, Rockville, Md.). The DNA is eluted from the paper in 10 mM Tris-HCl, pH 7.5, 1 mM EDTA by heating at 80° C. for 5 min. The concentration of the eluted DNA is approximately 1 ng/µl. One µl of this DNA is amplified in a 50 µl reaction as described in Example 2, incubating at 37° C. for 20 min. The concentration of the DNA in the completed reaction is 0.5 µg/µl, a 25,000-fold amplification. Aliquots of this DNA can be used directly for genotyping using PCR reactions; e.g. 1 µl in a 25 µl PCR reaction.

EXAMPLE 9

Detection of Contaminating DNA by Amplification Reaction

In order to characterize the level of contamination of DNA in an unknown sample, reactions are carried out as described in Example 2 using varying amounts of the unknown sample. As a control, a standard series of reactions are also carried out both in the absence of DNA and in the presence of 1, 10, 100 and 1,000 pg of a standard supercoiled plasmid DNA such as pUC18. The reactions are carried out at 37° C. for 15 min. The reaction mixtures are carried out in the presence of 20 cpm/pmole [$^3$H]TTP, and the amount of DNA synthesis in each sample is determined by measuring the amount of radioactivity taken up into DNA, as described in Example 1. Alternatively, DNA synthesis can be monitored in real time using a fluorescent probe (see Example 4). The amounts of DNA synthesized in the unknown samples are compared with the amounts of DNA synthesized in the standard reactions containing different initial concentrations of the known DNA in order to extrapolate the relative amount of contaminating DNA in the unknown sample.

EXAMPLE 10

Simple Molecule Amplification in Agarose

In accordance with the description above, in this example, single DNA molecules are amplified as individual foci embedded in a solid matrix, such as agarose. The amplified DNA is detected by fluorescence in the presence of the dye SYBR Green II (Molecular Probes, Eugene, Oreg.).

Reactions are carried out as described in Example 4. Two-fold concentrated reaction mixtures are prepared, and then diluted two-fold with a solution containing liquid 1% Sea-Plaque agarose (FMC Products, Rockland, Me.). The agarose is prepared in water and dissolved at 90° C., then cooled to 37° C. before mixing with the reaction mixtures. The reaction mixtures contain a final 1/80,000× concentration of SYBR Green II fluorescent dye, and varying amounts of supercoiled pUC18 DNA, ranging from none up to 100,000 molecules per µl. After mixing the agarose and the reaction mixture, the mixture is plated on a microscope slide, covered with a cover slip, and placed on ice to solidify the mixture. The slide is then heated at 37° C. and the progression of foci is monitored using a fluorescence microscope, exciting at a wavelength of 480 nM and observing the emission at 530 nM. In the absence of added DNA, approximately 20 foci are observed on a one cm$^2$ region, that correspond to the amplification of contaminating DNA. In the presence of increasing amounts of pUC18 DNA, the number of foci increasing proportionally, and thus correspond to amplification of the added DNA. Each foci corresponds to the amplification of a single DNA molecule, and thus is "clonal".

While the example below uses supercoiled pUC18 DNA as a template, one skilled in the art will recognize that other circular DNAs could be used. For example, if BAC DNA was digested with EcoRI, and then ligated, a population of circular fragments, or a "library", would be generated. If a splint oligonucleotide was ligated between the EcoRI sites, these could then serve as primer sites to sequence each insert in both directions. Using this strategy, all the amplified foci embedded on an agarose bed could be sequenced in a single dye-terminator sequencing reaction. After carrying out the sequencing reactions, the unincorporated dye terminators and the salts could be washed out of the agarose and each foci could be sequenced directly by injection into a capillary-based sequencing instrument such as the PE Biosystems 3700. This would allow one to generate a library of subclones of a large DNA fragment rapidly without the use of *E. coli* cells, and then to sequence all the fragments in a single sequencing reaction, that could be directly loaded onto a capillary sequencing instrument. This would represent a tremendous reduction in the scale of required reagents and human labor involved in cloning and sequencing fragments.

EXAMPLE 11

Overproduction and Purification of the 63-kDa T7 Gene 4 Protein

A preferred T7 gene 4 protein used in this invention is the 63-kDa form referred to as G4A$_{G64}$ in Mendelman et al., (*Proc. Natl. Acad. Sci. USA* 89:10638, 1992) and Mendelman et al., (*J. Biol. Chem.* 268:27208, 1993). It is the wild-type 63-kDa gene 4 protein except that the methionine at residue 64 has been replaced with a glycine to prevent initiation of synthesis of the 56-kDa form of the gene 4 protein. Expression of the T7 gene 4 in *E. coli* is toxic to the cells and must be kept tightly repressed when uninduced. Furthermore, when induced, the toxicity prevents efficient overproduction of the protein. It is known that mutants of gene 4 protein such as those in the nucleotide binding site eliminate this toxicity and result in much greater overproduction of the protein (Notarnicola and Richardson, *J. Biol. Chem.* 268:27198, 1993). This observation suggests that it is the potent TTPase activity of the wild-type gene 4 protein that is responsible for the toxicity. Thus one method to increase the amount of wild-type gene 4 protein overproduced in cells is to coexpress another molecule that will bind to the wild-type gene 4 protein and inhibit its TTPase activity. Three possible classes of molecules that may accomplish this are protein, RNA and DNA aptamers (Cohen et al., *Proc. Natl. Acad. Sci. USA* 95:14272, 1998; Famulok and Jenne, *Curr. Opin. Chem. Biol.* 2:320, 1998), which can be selected for from libraries on the basis of either binding to wild-type gene 4 protein in vitro, or inhibit the toxicity of its production in vivo.

An alternative approach is to coexpress a fragment of gene 4 that interferes with the activity of the wild-type gene 4 protein. The 295 residue carboxyl-terminal fragment of gene 4 protein from arginine 271 to the end of the gene has this property; in vitro it inhibits the wild-type gene 4 protein's TTPase activity, and in vivo it reduces the toxicity of the wild-type gene 4 and increases the overproduction of the wild-type gene 4 protein by at least 10-fold (Guo et al., *J. Biol. Chem.* 274:30303, 1999). It is likely that other carboxyl-terminal fragments of the gene 4 will have a similar effect.

To overproduce the $G4A_{64A}$ form of the gene 4 protein, the plasmid pGP4A/4E-1 whose sequence is shown in FIG. 1 (SEQ. ID. NO. 1), was used. It expresses both the $G4A_{64A}$ gene 4 and the gene 4 fragment initiating at codon 271, both from T7 RNA polymerase promoters. The two genes are in tandem, with the $G4A_{64A}$ expressed upstream of the gene 4 fragment that starts at codon 271 (see FIG. 1). pGP4A/4E-1 was used to transform the *E. coli* cells BL21/DE3 (Novagen, Inc., Madison, Wis.) and selected for by plating on agar plates containing 50 μg/ml kanamycin. The cells were grown in LB media containing 50 μg/ml kanamycin at 30° C. When the cell density reached $A_{590}=1$, the gene 4 proteins were induced by the addition of 0.5 mM IPTG. After inducing for 3 hours at 30° C., the cells were harvested and frozen at −80° C.

The 63-kDa gene 4 protein was purified by the procedure described by Notarnicola et al. (*J. Biol. Chem.* 270:20215, 1995). Briefly, the cells were lysed by the addition of lysozyme and by sonication. After the cell debris was removed by centrifugation, the 63-kDa gene 4 protein was precipitated by the addition of 15% polyethylene glycol 4000. After resuspension of the precipitate, the gene 4 protein was purified by phosphocellulose chromatography. Finally, the pool of the fractions containing gene 4 protein from the phosphocellulose column was purified by ATP-agarose affinity chromatography. The gene 4 protein fragment present in the extract separates from the $G4A_{64A}$ gene 4 protein both in the PEG precipitation, the phosphocellulose chromatography, and the ATP affinity chromatography. From 10 liters of induced cell culture, 100 mg of pure $G4A_{64A}$ gene 4 protein were obtained.

Other embodiments within the scope of the following claims.

What is claimed is:

1. A method of amplifying a template DNA molecule, said method comprising incubating said template DNA molecule in an in vitro reaction mixture comprising:
   wild-type T7 DNA polymerase,
   a T7 DNA polymerase modified to have reduced 3' to 5' exonuclease activity,
   the 63-kDa form of a gene 4 protein from bacteriophage T7, and
   a single-stranded DNA binding protein from *Escherichia coli* at a constant temperature to produce amplified product,
   wherein the amplification reaction is conducted in the absence of exogenously added oligonucleotide primers, and
   wherein the amount of the amplified product is at least 10-fold greater than the amount of template DNA put into the mixture.

2. The method of claim 1, wherein the molar ratio of said T7 DNA polymerase modified to have reduced 3' to 5' exonuclease activity to said wild-type T7 DNA polymerase is greater than 1.

3. The method of claim 1, wherein the molar ratio of said T7 DNA polymerase modified to have reduced 3' to 5' exonuclease activity to said wild-type T7 DNA polymerase is approximately 20:1.

4. The method of claim 1, wherein said constant temperature is less than 45° C.

5. The method of claim 1, wherein said constant temperature is less than 40° C.

6. The method of claim 1, wherein said constant temperature is about 37° C.

7. The method of claim 1, wherein said method is performed under conditions such that the amount of amplified product is at least 100-fold greater than the amount of template DNA put into the mixture.

8. The method of claim 1, wherein said method is performed under conditions such that the amount of amplified product is at least 1,000-fold greater than the amount of template DNA put into the mixture.

9. The method of claim 1, wherein said method is performed under conditions such that the amplification of template DNA is exponential.

10. The method of claim 1, wherein the reaction mixture further comprises one or more reagents selected from the group consisting of a nucleoside diphosphokinase, an inorganic pyrophosphatase, an ATP regeneration system, a double-stranded exonuclease, a T7 single-stranded DNA binding protein and a ligase.

11. The method of claim 1, wherein the reaction mixture further comprises a nucleoside diphosphokinase.

12. The method of claim 1, wherein the reaction mixture further comprises an inorganic pyrophosphatase.

13. The method of claim 1, wherein the reaction mixture further comprises an ATP regeneration system.

14. The method of claim 13, wherein said ATP regeneration system comprises a combination of creatine kinase and phosphocreatine.

15. The method of claim 1, wherein the reaction mixture further comprises a ligase.

16. The method of claim 15, wherein said ligase is bacteriophage T7 DNA ligase.

17. The method of claim 1, wherein the reaction mixture further comprises a double-stranded exonuclease.

18. The method of claim 1, wherein the reaction mixture further comprises one or more additives selected from the group consisting of potassium glutamate, DMSO and dextran polymer.

19. The method of claim 10, wherein said method is performed under conditions such that the amount of amplified product is at least 100-fold greater than the amount of template DNA put into the mixture.

20. The method of claim 10, wherein said method is performed under conditions such that the amount of amplified product is at least 1000-fold greater than the amount of template DNA put into the mixture.

21. The method of claim 10, wherein said method is performed under conditions such that the amount of amplified product is at least 100,000-fold greater than the amount of template DNA put into the mixture.

22. The method of claim 10, wherein said method is performed under conditions such that the amount of amplified product is at least 1,000,000-fold greater than the amount of template DNA put into the mixture.

23. The method of claim 10, wherein said method is performed under conditions such that the amount of amplified product is at least 10,000,000-fold greater than the amount of template DNA put into the mixture.

24. The method of claim 10, wherein said method is performed under conditions such that the amplification of template DNA is exponential.

25. The method of claim 1, wherein said T7 DNA polymerase modified to have reduced 3' to 5' exonuclease activity is Δ28 T7 DNA polymerase.

26. A method of amplifying a template DNA molecule, said method comprising incubating said template DNA molecule in an in vitro reaction mixture comprising:
   wild-type T7 DNA polymerase,
   Δ28 T7 DNA polymerase,
   the 63-kDa form of a gene 4 protein from bacteriophage T7,
   a single-stranded DNA binding protein from *Escherichia coli*, and
   one or more components selected from the group consisting of nucleoside diphosphokinase, T7 single-stranded DNA binding protein, T7 gene 6 exonuclease, T7 DNA ligase, and a combination of creatine kinase and phosphocreatine, at a constant temperature to produce amplified product, wherein the amplification reaction is conducted in the absence of exogenously added oligonucleotide primers, and wherein the amount of the amplified product is at least 10-fold greater than the amount of template DNA put into the mixture.

27. The method of claim 26, wherein the reaction mixture further comprises one or more additives selected from the group consisting of potassium glutamate, DMSO and dextran polymer.

28. The method of claim 26, wherein said constant temperature is between 10° C. and 50° C.

29. The method of claim 26, wherein said constant temperature is about 37° C.

30. The method of claim 26, wherein said method is performed under conditions such that the amount of amplified product is at least 100-fold greater than the amount of template DNA put into the mixture.

31. The method of claim 26, wherein said method is performed under conditions such that the amount of amplified product is at least 1000-fold greater than the amount of template DNA put into the mixture.

32. The method of claim 26, wherein said method is performed under conditions such that the amount of amplified product is at least 100,000-fold greater than the amount of template DNA put into the mixture.

33. The method of claim 26, wherein said method is performed under conditions such that the amount of amplified product is at least 1,000,000-fold greater than the amount of template DNA put into the mixture.

34. The method of claim 26, wherein said method is performed under conditions such that the amount of amplified product is at least 10,000,000-fold greater than the amount of template DNA put into the mixture.

* * * * *

UNITED STATES PATENT AND TRADEMARK OFFICE
CERTIFICATE OF CORRECTION

PATENT NO. : 8,709,724 B2
APPLICATION NO. : 10/813693
DATED : April 29, 2014
INVENTOR(S) : Tabor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 747 days.

Signed and Sealed this
Twenty-eighth Day of July, 2015

Michelle K. Lee
*Director of the United States Patent and Trademark Office*

SEQUENCE LISTING

```
<160> NUMBER OF SEQ ID NOS: 6

<210> SEQ ID NO 1
<211> LENGTH: 8970
<212> TYPE: DNA
<213> ORGANISM: Artificial Sequence
<220> FEATURE:
<223> OTHER INFORMATION: Description of Artificial Sequence:
      Bacteriaphage PGP 4A/E1

<400> SEQUENCE: 1
atggacaatt cgcacgattc cgatagtgta tttctttacc acattccttg tgacaactgt        60
gggagtagtg atgggaactc gctgttctct gacggacaca cgttctgcta cgtatgcgag       120
aagtggactg ctggtaatga agacactaaa gagagggctt caaaacggaa accctccggc       180
ggaaagcccg ggacttacaa cgtgtggaac ttcggggaat ccaatggacg ctactccgcg       240
ttaactgcga gaggaatctc caaggaaacc tgtcagaagg ctggctactg gattgccaaa       300
gtagacggtg tgatgtacca agtggctgac tatcgggacc agaacggcaa cattgtgagt       360
cagaaggttc gagataaaga taagaacttt aagaccactg gtagtcacaa gagtgacgct       420
ctgttcggga agcacttgtg gaatggtggt aagaagattg tcgttacaga aggtgaaatc       480
gacatgctta ccgtgatgga acttcaagac tgtaagtatc ctgtagtgtc gttgggtcac       540
ggtgcctctg ccgctaagaa gacatgcgct gccaactacg aatactttga ccagttcgaa       600
cagattatct taatgttcga tatggacgaa gcagggcgca aagcagtcga agaggctgca       660
caggttctac ctgctggtaa ggtacgagtg gcagttcttc cgtgtaagga tgcaaacgag       720
tgtcacctaa atggtcacga ccgtgaaatc atggagcaag tgtggaatgc tggtccttgg       780
attcctgatg gtgtggtatc ggctctttcg ttacgtgaac gaatccgtga gcacctatcg       840
tccgaggaat cagtaggttt actttcagt ggctgcactg gtatcaacga taagaccta       900 ggtgcccgtg gtggtgaagt cattatggtc acttccggtt ccggtatggg taagtcaacg       960
ttcgtccgtc aacaagctct acaatggggc acagcgatgg gcaagaaggt aggcttagcg      1020
```

```
atgcttgagg agtccgttga ggagaccgct gaggacctta taggtctaca caaccgtgtc    1080
cgactgagac aatccgactc actaaagaga gagattattg agaacggtaa gttcgaccaa    1140
tggttcgatg aactgttcgg caacgatacg ttccatctat atgactcatt cgccgaggct    1200
gagacggata gactgctcgc taagctggcc tacatgcgct caggcttggg ctgtgacgta    1260
atcattctag accacatctc aatcgtcgta tccgcttctg gtgaatccga tgagcgtaag    1320
atgattgaca acctgatgac caagctcaaa gggttcgcta agtcaactgg ggtggtgctg    1380
gtcgtaattt gtcaccttaa gaacccagac aaaggtaaag cacatgagga aggtcgcccc    1440
gtttctatta ctgacctacg tggttctggc gcactacgcc aactatctga tactattatt    1500
gcccttgagc gtaatcagca aggcgatatg cctaaccttg tcctcgttcg tattctcaag    1560
tgccgcttta ctggtgatac tggtatcgct ggctacatgg aatacaacaa ggaaaccgga    1620
tggcttgaac catcaagtta ctcaggggaa gaagagtcac actcagagtc aacagactgg    1680
tccaacgaca ctgacttctg acaggattct tgatgacttt ccagacgact acgagaagtt    1740
tcgctggaga gtcccattct aatacgactc actaaaggag acacaccatg ttcaaactga    1800
ttaagaagtt aggccaactg ctggttcgta tgtacaacgt ggaagccaag cgactgaacg    1860
atgaggctcg taaagaggcc acacagtcac gcgctctggc gattcgctcc aaaactggtt    1920
ttgcgcttac cccaaccaac aggggatttg ctgctttcca ttgagcctgt ttctctgcgc    1980
gacgttcgcg gcggcgtgtt tgtgcatcca tctggattct cctgtcagtt agctttggtg    2040
gtgtgtggca gttgtagtcc tgaacgaaaa ccccccgcga ttggcacatt ggcagctaat    2100
ccggaatcgc acttacggcc aatgcttcgt ttcgtatcac acaccccaaa gccttctgct    2160
ttgaatgctg cccttcttca gggcttaatt tttaagagcg tcaccttcat ggtggtcagt    2220
gcgtcctgct gatgtgctca gtatcaccgc cagtggtatt tatgtcaaca ccgccagaga    2280
taatttatca ccgcagatgg ttatctgtat gttttttata tgaatttatt ttttgcaggg    2340
gggcattgtt tggtaggtga gagatccggc tgctaacaaa gcccgaaagg aagctgagtt    2400
ggctgctgcc accgctgagc aataactagc ataaccccct ggggcctcta acgggtctt    2460
gagggttttt ttgctgaaag gaggaactat atccggatat cccgcaagag gcccggcagt    2520
accggcataa ccaagcctat gcctacagca tccagggtga cggtgccgag gatgacgatg    2580
agcgcattgt tagatttcat acacggtgcc tgactgcgtt agcaatttaa ctgtgataaa    2640
ctaccgcatt aaagcttgcg gccgcactcg acgaaccctt cggatctcga tcccgcgaaa    2700
ttaatacgac tcactatagg gagaccacaa cggtttccct ctagaaataa ttttgtttaa    2760
ctttaagaag gagatataca tatgcgtgaa cgaatccgtg agcacctatc gtccgaggaa    2820
tcagtaggtt acttttcag tggctgcact ggtatcaacg ataagacctt aggtgcccgt    2880
ggtggtgaag tcattatggt cacttccggt tccggtatgg gtaagtcaac gttcgtccgt    2940
caacaagctc tacaatgggg cacagcgatg ggcaagaagg taggcttagc gatgcttgag    3000
gagtccgttg aggagaccgc tgaggacctt ataggtctac acaaccgtgt ccgactgaga    3060
caatccgact cactaaagag agagattatt gagaacggta agttcgacca atggttcgat    3120
gaactgttcg gcaacgatac gttccatcta tatgactcat cgccgaggc tgagacggat    3180
agactgctcc taagctggc ctacatgcgc tcaggcttgg gctgtgacgt aatcattcta    3240
gaccacatct caatcgtcgt atccgcttct ggtgaatccg atgagcgtaa gatgattgac    3300
aacctgatga ccaagctcaa agggttcgct aagtcaactg gggtggtgct ggtcgtaatt    3360
tgtcacctta agaacccaga caaaggtaaa gcacatgagg aaggtcgccc cgtttctatt    3420
```

```
actgacctac gtggttctgg cgcactacgc caactatctg atactattat tgcccttgag   3480
cgtaatcagc aaggcgatat gcctaacctt gtcctcgttc gtattctcaa gtgccgcttt   3540
actggtgata ctggtatcgc tggctacatg aatacaaca aggaaaccgg atggcttgaa    3600
ccatcaagtt actcagggga agaagagtca cactcagagt caacagactg gtccaacgac   3660
actgacttct gaggatccac tagtaacggc cgccagtgtg ctggaattct gcagatatcc   3720
atcacactgg cggccgctcg agcaccacca ccaccaccac tgagatccgg ctgctaacaa   3780
agcccgaaag gaagctgagt tggctgctgc caccgctgag caataactag cataacccct   3840
tggggcctct aaacgggtct tgaggggttt tttgctgaaa ggaggaacta tatccggatt   3900
ggcgaatggg acgcgccctg tagcggcgca ttaagcgcgg cgggtgtggt ggttacgcgc   3960
agcgtgaccg ctacacttgc cagcgcccta gcgcccgctc ctttcgcttt cttcccttcc   4020
tttctcgcca cgttcgccgg ctttccccgt caagctctaa atcgggggct ccctttaggg   4080
ttccgattta gtgctttacg gcacctcgac cccaaaaaac ttgattaggg tgatggttca   4140
cgtagtgggc catcgccctg atagacggtt tttcgccctt tgacgttgga gtccacgttc   4200
tttaatagtg gactcttgtt ccaaactgga acaacactca accctatctc ggtctattct   4260
tttgatttat aagggatttt gccgatttcg gcctattggt taaaaaatga gctgatttaa   4320
caaaaattta acgcgaattt taacaaaata ttaacgttta caatttcagg tggcactttt   4380
cggggaaatg tgcgcggaac ccctatttgt ttatttttct aaatacattc aaatatgtat   4440
ccgctcatga attaattctt agaaaaactc atcgagcatc aaatgaaact gcaatttatt   4500
catatcagga ttatcaatac catattttg aaaaagccgt ttctgtaatg aaggagaaaa    4560
ctcaccgagg cagttccata ggatggcaag atcctggtat cggtctgcga ttccgactcg   4620
tccaacatca atacaaccta ttaatttccc ctcgtcaaaa ataaggttat caagtgagaa   4680
atcaccatga gtgacgactg aatccggtga gaatggcaaa agtttatgca tttctttcca   4740
gacttgttca acaggccagc cattacgctc gtcatcaaaa tcactcgcat caaccaaacc   4800
gttattcatt cgtgattgcg cctgagcgag acgaaatacg cgatcgctgt taaaaggaca   4860
attacaaaca ggaatcgaat gcaaccggcg caggaacact gccagcgcat caacaatatt   4920
ttcacctgaa tcaggatatt cttctaatac ctggaatgct gttttcccgg ggatcgcagt   4980
ggtgagtaac catgcatcat caggagtacg gataaaatgc ttgatggtcg gaagaggcat   5040
aaattccgtc agccagttta gtctgaccat ctcatctgta acatcattgg caacgctacc   5100
tttgccatgt ttcagaaaca actctggcgc atcgggcttc ccatacaatc gatagattgt   5160
cgcacctgat tgcccgacat tatcgcgagc ccatttatac ccatataaat cagcatccat   5220
gttggaattt aatcgcggcc tagagcaaga cgtttcccgt tgaatatggc tcataacacc   5280
ccttgtatta ctgtttatgt aagcagacag ttttattgtt catgaccaaa atcccttaac   5340
gtgagttttc gttccactga gcgtcagacc ccgtagaaaa gatcaaagga tcttcttgag   5400
atcctttttt tctgcgcgta atctgctgct tgcaaacaaa aaaaccaccg ctaccagcgg   5460
tggtttgttt gccggatcaa gagctaccaa ctctttttcc gaaggtaact ggcttcagca   5520
gagcgcagat accaaatact gtccttctag tgtagccgta gttaggccac cacttcaaga   5580
actctgtagc accgcctaca tacctcgctc tgctaatcct gttaccagtg gctgctgcca   5640
gtggcgataa gtcgtgtctt accgggttgg actcaagacg atagttaccg gataaggcgc   5700
agcggtcggg ctgaacgggg ggttcgtgca cacagcccag cttggagcga acgacctaca   5760
ccgaactgag atacctacag cgtgagctat gagaaagcgc cacgcttccc gaagggagaa   5820
```

```
aggcggacag gtatccggta agcggcaggg tcggaacagg agagcgcacg agggagcttc    5880 caggggaaa cgcctggtat ctttatagtc ctgtcgggtt tcgccacctc tgacttgagc     5940
gtcgattttt gtgatgctcg tcagggggc ggagcctatg gaaaaacgcc agcaacgcgg     6000 ccttttacg gttcctggcc ttttgctggc cttttgctca catgttcttt cctgcgttat     6060 ccctgattc tgtggataac cgtattaccg cctttgagtg agctgatacc gctcgccgca     6120
gccgaacgac cgagcgcagc gagtcagtga gcgaggaagc ggaagagcgc ctgatgcggt     6180
attttctcct tacgcatctg tgcggtattt cacaccgcat atatggtgca ctctcagtac     6240
aatctgctct gatgccgcat agttaagcca gtatacactc cgctatcgct acgtgactgg     6300
gtcatggctg cgccccgaca cccgccaaca cccgctgacg cgccctgacg gcttgtctg     6360 ctcccggcat ccgcttacag acaagctgtg accgtctccg ggagctgcat gtgtcagagg     6420
ttttcaccgt catcaccgaa acgcgcgagg cagctgcggt aaagctcatc agcgtggtcg     6480
tgaagcgatt cacagatgtc tgcctgttca tccgcgtcca gctcgttgag ttctccaga     6540 agcgttaatg tctggcttct gataaagcgg gccatgttaa gggcggtttt ttcctgtttg     6600
gtcactgatg cctccgtgta agggggattt ctgttcatgg gggtaatgat accgatgaaa     6660
cgagagagga tgctcacgat acgggttact gatgatgaac atgcccggtt actggaacgt     6720
tgtgagggta acaactggc ggtatggatg cggcgggacc agagaaaaat cactcagggt      6780
caatgccagc gcttcgttaa tacagatgta ggtgttccac agggtagcca gcagcatcct     6840
gcgatgcaga tccggaacat aatggtgcag ggcgctgact ccgcgtttc cagactttac      6900 gaaacacgga aaccgaagac cattcatgtt gttgctcagg tcgcagacgt tttgcagcag     6960
cagtcgcttc acgttcgctc gcgtatcggt gattcattct gctaaccagt aaggcaaccc     7020
cgccagccta gccgggtcct caacgacagg agcacgatca tgcgcacccg tggggccgcc     7080
atgccggcga taatggcctg cttctcgccg aaacgtttgg tggcgggacc agtgacgaag     7140
gcttgagcga gggcgtgcaa gattccgaat accgcaagcg acaggccgat catcgtcgcg     7200
ctccagcgaa agcggtcctc gccgaaaatg acccagagcg ctgccggcac ctgtcctacg     7260
agttgcatga taaagaagac agtcataagt gcggcgacga tagtcatgcc ccgcgcccac     7320
cggaaggagc tgactgggtt gaaggctctc aagggcatcg gtcgagatcc cggtgcctaa     7380
tgagtgagct aacttacatt aattgcgttg cgctcactgc ccgctttcca gtcgggaaac     7440
ctgtcgtgcc agctgcatta tgaatcggc caacgcgcgg ggagaggcgg tttgcgtatt      7500
gggcgccagg gtggtttttc ttttcaccag tgagacgggc aacagctgat tgcccttcac     7560
cgcctggccc tgagagagtt gcagcaagcg gtccacgctg gtttgcccca gcaggcgaaa     7620
atcctgtttg atggtggtta acggcgggat ataacatgag ctgtcttcgg tatcgtcgta     7680
tcccactacc gagatatccg caccaacgcg cagcccggac tcggtaatgg cgcgcattgc     7740
gcccagcgcc atctgatcgt tggcaaccag catcgcagtg ggaacgatgc cctcattcag     7800
catttgcatg gtttgttgaa accggacat ggcactccag tcgccttccc gttccgctat      7860
cggctgaatt tgattgcgag tgagatattt atgccagcca gcagacgca gacgcgccga      7920 gacagaactt aatgggcccg ctaacagcgc gatttgctgg tgacccaatg cgaccagatg     7980
ctccacgccc agtcgcgtac cgtcttcatg ggagaaaata atactgttga tgggtgtctg     8040
gtcagagaca tcaagaaata cgccggaac attagtgcag gcagcttcca cagcaatggc      8100
atcctggtca tccagcggat agttaatgat cagcccactg acgcgttgcg cgagaagatt     8160
gtgcaccgcc gctttacagg cttcgacgcc gcttcgttct accatcgaca ccaccacgct     8220
```

```
ggcacccagt tgatcggcgc gagatttaat cgccgcgaca atttgcgacg gcgcgtgcag    8280
ggccagactg gaggtggcaa cgccaatcag caacgactgt tgcccgcca gttgttgtgc     8340 cacgcggttg ggaatgtaat tcagctccgc catcgccgct tccactttt cccgcgtttt     8400 cgcagaaacg tggctggcct ggttcaccac gcgggaaacg gtctgataag agacaccggc    8460
atactctgcg acatcgtata acgttactgg tttcacattc accaccctga attgactctc    8520
ttccgggcgc tatcatgcca taccgcgaaa ggttttgcgc cattcgatgg tgtccgggat    8580
ctcgacgctc tcccttatgc gactcctgca ttaggaagca gcccagtagt aggttgaggc    8640
cgttgagcac cgccgccgca aggaatggtg catgcaagga gatggcgccc aacagtcccc    8700
cggccacggg gcctgccacc atacccacgc cgaaacaagc gctcatgagc ccgaagtggc    8760
gagcccgatc ttccccatcg gtgatgtcgg cgatataggc gccagcaacc gcacctgtgg    8820
cgccggtgat gccggccacg atgcgtccgg cgtagaggat cgagatctcg atcccgcgaa    8880
attaatacga ctcactatag gggaattgtg agcggataac aattcccctc tagaaataat    8940
tttgtttaac tttaagaagg agatatacat                                     8970
```

```
<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgcggtacac cgacgtcaa                                                 19

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cgcggtacac cgacttaat                                                 19

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtcggtgtac                                                           10

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
taatacgact cactataggg cga                                            23
```

```
<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
catacgattt aggtgacact atag                                              24
```